(12) United States Patent
Slager et al.

(10) Patent No.: US 8,241,921 B2
(45) Date of Patent: Aug. 14, 2012

(54) ACTIVE AGENT ELUTING MATRICES WITH PARTICULATES

(75) Inventors: Joram Slager, St. Louis Park, MN (US); Aron B. Anderson, Minnetonka, MN (US)

(73) Assignee: Surmodics, Inc., Eden Prairie, MN (US)

( * ) Notice: Subject to any disclaimer, the term of this patent is extended or adjusted under 35 U.S.C. 154(b) by 190 days.

(21) Appl. No.: 12/647,780

(22) Filed: Dec. 28, 2009

(65) Prior Publication Data

US 2010/0166829 A1 Jul. 1, 2010

Related U.S. Application Data

(62) Division of application No. 11/824,340, filed on Jun. 28, 2007, now Pat. No. 7,638,344.

(60) Provisional application No. 60/806,030, filed on Jun. 28, 2006.

(51) Int. Cl.
*G01N 33/558* (2006.01)

(52) U.S. Cl. .................................................. 436/514

(58) Field of Classification Search .................. None
See application file for complete search history.

(56) References Cited

U.S. PATENT DOCUMENTS

| | | | |
|---|---|---|---|
| 4,373,009 A | 2/1983 | Winn | |
| 4,638,045 A | 1/1987 | Kohn et al. | |
| 5,089,606 A * | 2/1992 | Cole et al. ................ | 536/54 |
| 5,252,701 A | 10/1993 | Jarrett et al. | |
| 5,395,626 A * | 3/1995 | Kotwal et al. ............. | 424/472 |
| 5,571,531 A | 11/1996 | McDermott et al. | |
| 5,645,593 A | 7/1997 | Woods et al. | |
| 5,660,854 A | 8/1997 | Haynes et al. | |
| 5,879,713 A | 3/1999 | Roth et al. | |
| 5,980,948 A | 11/1999 | Goedemoed et al. | |
| 6,143,037 A | 11/2000 | Goldstein et al. | |
| 6,214,901 B1 | 4/2001 | Chudzik et al. | |
| 6,228,393 B1 | 5/2001 | DiCosmo et al. | |
| 6,261,537 B1 | 7/2001 | Klaveness et al. | |
| 6,303,148 B1 | 10/2001 | Hennink et al. | |
| 6,497,729 B1 | 12/2002 | Moussy et al. | |
| 6,503,556 B2 | 1/2003 | Harish et al. | |
| 6,669,980 B2 | 12/2003 | Hansen | |
| 6,673,385 B1 | 1/2004 | Ding et al. | |
| 6,703,040 B2 | 3/2004 | Katsarava et al. | |
| 7,491,234 B2 * | 2/2009 | Palasis et al. ............. | 623/1.42 |
| 7,638,344 B2 * | 12/2009 | Slager et al. .............. | 436/514 |
| 2002/0041899 A1 | 4/2002 | Chudzik et al. | |
| 2002/0138154 A1 | 9/2002 | Li et al. | |
| 2002/0168394 A1 | 11/2002 | Hossainy et al. | |
| 2002/0188037 A1 | 12/2002 | Chudzik et al. | |
| 2003/0064965 A1 | 4/2003 | Richter | |
| 2003/0078647 A1 | 4/2003 | Vallana et al. | |
| 2003/0093107 A1 | 5/2003 | Parsonage et al. | |
| 2003/0129130 A1 | 7/2003 | Guire et al. | |
| 2004/0023028 A1 | 2/2004 | Yaszemski et al. | |
| 2004/0033241 A1 | 2/2004 | Donovan | |
| 2004/0062875 A1 | 4/2004 | Chappa et al. | |
| 2004/0106987 A1 * | 6/2004 | Palasis et al. ............. | 623/1.42 |
| 2004/0133155 A1 | 7/2004 | Varner et al. | |
| 2005/0019371 A1 | 1/2005 | Anderson et al. | |
| 2005/0037047 A1 | 2/2005 | Song | |
| 2005/0095267 A1 | 5/2005 | Campbell et al. | |
| 2005/0119723 A1 | 6/2005 | Peacock, III | |
| 2005/0181015 A1 * | 8/2005 | Zhong ........................ | 424/426 |
| 2005/0208095 A1 | 9/2005 | Hunter et al. | |
| 2005/0220843 A1 | 10/2005 | DeWitt et al. | |
| 2005/0220853 A1 * | 10/2005 | Dao et al. .................. | 424/449 |
| 2005/0244459 A1 | 11/2005 | DeWitt et al. | |
| 2005/0255142 A1 * | 11/2005 | Chudzik et al. ........... | 424/426 |
| 2005/0261283 A1 | 11/2005 | Sukhatme et al. | |
| 2006/0088653 A1 | 4/2006 | Chappa | |
| 2007/0071792 A1 * | 3/2007 | Varner et al. .............. | 424/427 |
| 2007/0128343 A1 | 6/2007 | Chappa | |
| 2007/0260054 A1 | 11/2007 | Chudzik | |
| 2007/0276473 A1 | 11/2007 | Llanos et al. | |

FOREIGN PATENT DOCUMENTS

| | | |
|---|---|---|
| EP | 0 289 996 | 11/1988 |
| WO | 89/09246 | 10/1989 |
| WO | 93/06925 | 4/1993 |
| WO | 98/58990 | 12/1998 |
| WO | 01/89595 | 11/2001 |
| WO | 2005/018606 | 3/2005 |
| WO | 2005/099667 | 10/2005 |

OTHER PUBLICATIONS

PCT Search Report for International Application PCT/US2007/015075 mailed Jun. 12, 2007.
Specification Sheet: Amylose from potato, Sigma-Aldrich Product No. A0512.
Sarko, et al., (1964) "*Water-Soluable Amylose: Preparation and Properties*", Journal of Applied Polymer Science 8:1343-1355.

* cited by examiner

*Primary Examiner* — Ann Lam
(74) *Attorney, Agent, or Firm* — Kagan Binder, PLLC

(57) ABSTRACT

The present invention is directed to polymeric matrices for the controlled release of a hydrophilic bioactive agent. Generally, the elution control matrix includes a polymeric matrix having a first polymer and a plurality of microparticles that include the hydrophilic bioactive agent. In one embodiment, the matrix includes a polymer comprising hydrophilic and hydrophobic portions. In another embodiment, the microparticles include a crosslinked hydrophilic polymer.

21 Claims, 10 Drawing Sheets

Figure 2:
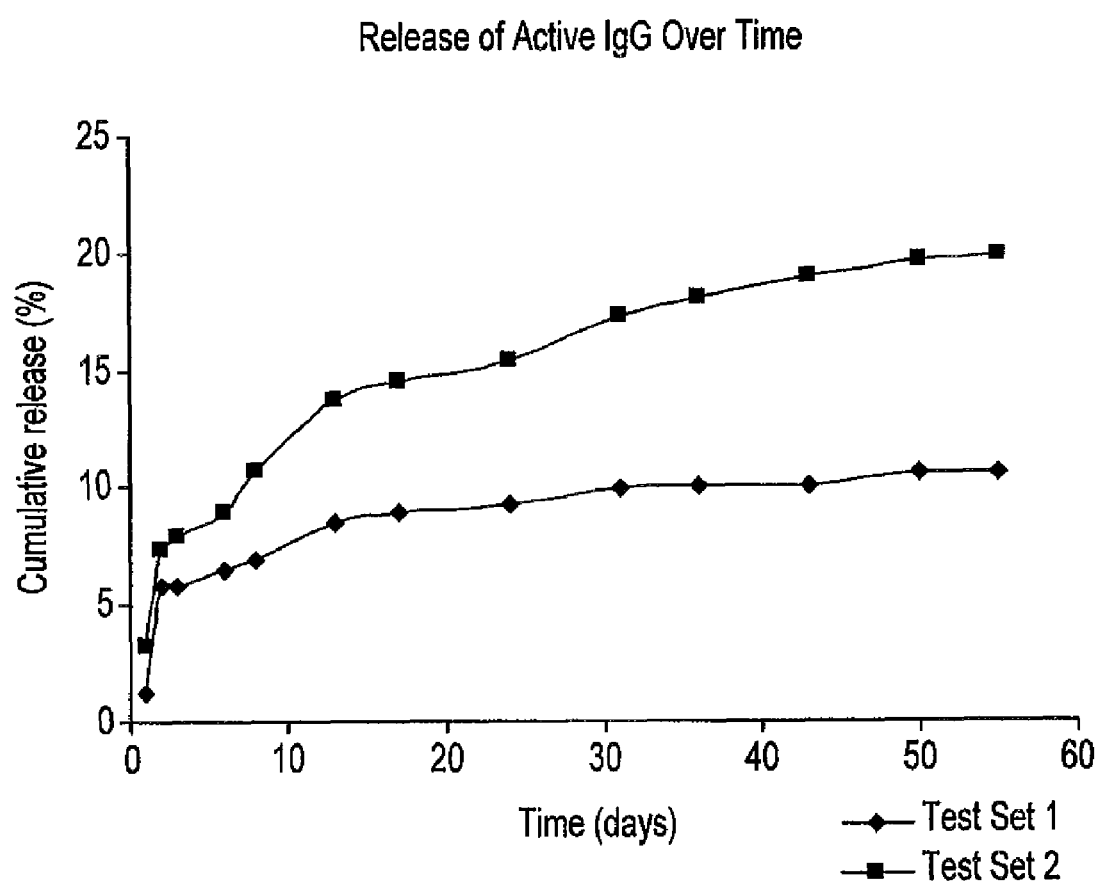

Release of active Rabbit IgG-anti goat from particle spray on long coils (measured with ELISA)

Fig. 1

Particle spray on Ivek, IgG at 40% w/w loading

- ◆ 1. PBMA/PEVA 1:1    ■ 2. PBMA/PEVA 1:1    ● 3. PBMA/PEVA 1:1
- △ 4. PBMA/PEVA 1:4    ○ 5. PBMA/PEVA 1:4    □ 6. PBMA/PEVA 1:4

Fig. 4

Particle Spray Coating of F(ab) from coils

- 300 ug of F(ab) microparticle loaded on each coil
- Coatings contain pBMA/pEVA, PEG$_{1000}$-45PBT-55 and Parylene

Fig. 8

ACTIVE AGENT ELUTING MATRICES WITH PARTICULATES

CROSS-REFERENCE TO RELATED APPLICATION

The present non-provisional patent Application is a divisional of U.S. patent application Ser. No. 11/824,340, filed on Jun. 28, 2007, now U.S. Pat. No. 7,638,344 which Application claims priority under 35 USC 119(e) from United States Provisional Patent Application having Ser. No. 60/806,030, filed on Jun. 28, 2006, and titled ACTIVE AGENT ELUTING COATINGS WITH PARTICULATES; both of which are fully incorporated herein by reference.

FIELD OF THE INVENTION

The present invention relates to polymeric matrices for hydrophilic drug delivery and related methods. More specifically, the present invention relates to polymeric matrices containing particulates and related methods.

BACKGROUND OF THE INVENTION

Therapeutic benefits can be achieved in some instances by providing a bioactive agent to a specific target tissue, instead of systemically. This is because the effect of the agent on the target tissue can be maximized while the side effects on other tissues can be minimized. Therapeutic benefits can also be achieved by providing a bioactive agent to a subject in a manner that provides controlled release of the bioactive agent. Controlled release of a bioactive agent can allow the concentration of the bioactive agent at the target tissue site to remain at a more consistent therapeutic level.

One technique for providing controlled-release site-specific drug delivery is to use a bioactive agent-eluting coating system disposed on a medical device. The coating can serve to control the rate at which the bioactive agent is eluted. In addition, because the coating is disposed on a medical device and because the medical device can be positioned as desired within the body of a patient, the delivery of the bioactive agent can be site-specific.

However, some types of bioactive agents may degrade or otherwise lose their activity if they are exposed to solvents used to apply coatings onto a substrate. In addition, some coating systems may not provide desired elution rate control of specific bioactive agents.

Accordingly, there is a need for polymeric matrices and their preparation, such as coatings, that can preserve the activity of bioactive agents. There is also a need for polymeric matrices that can provide elution rate control of bioactive agents as desired.

Some bioactive agents, such as proteins, exhibit activity that depends on their tertiary structure. Tertiary structure can be influenced by various factors external to the bioactive agent itself including temperature, solvent, other solutes, accessory molecules (such as chaperonins) and the like. Therefore, bioactive agent activity can inadvertently be degraded or even eliminated as a result of the handling conditions the bioactive agent is subjected to.

The process of putting a bioactive agent into a matrix forming solution and then disposing that solution upon a substrate (for example, by spraying) can involve exposure to a variety of solvents, exposure to other molecules, and exposure to varying temperatures. Because of their potential effect on the tertiary structure of a molecule, all of these conditions can potentially adversely affect the activity of the bioactive agent.

One approach to protecting the activity of a bioactive agent is to formulate it as a microparticle. As a microparticle, the bioactive agent can be protected during the process of dispersing it in a polymeric solution and applying it on to a substrate.

SUMMARY OF THE INVENTION

The present invention relates to polymeric matrices with microparticles, which are useful for the delivery of a bioactive agent to a subject.

In an embodiment, the invention includes an elution control matrix that can release a hydrophilic bioactive agent in a controlled manner. The elution control matrix comprises a polymeric matrix formed of at least a first polymer that is hydrophobic, a second polymer comprising hydrophobic and hydrophilic segments, and a plurality of microparticles dispersed in the matrix, the microparticles comprising a hydrophilic bioactive agent.

The first polymeric material provides a framework in which the microparticles are held and which, in some aspects, can be suitable as a coated layer on a surface of an implantable device. The microparticles are dispersed in the matrix, and can release the hydrophilic bioactive agent when the elution matrix is placed in an eluting environment. The hydrophilic bioactive agent, being in the form of microparticles, can be dispersed throughout the matrix in discrete microdomains. For hydrophilic bioactive agents, use of microparticles is advantageous over other matrix-forming processes that may result in the hydrophilic bioactive agent becoming aggregated or grossly non-dispersed in the matrix. Furthermore, the microparticles can provide an aspect of the control over release of the bioactive agent. Optionally, the microparticles can be associated with a polymer (such as one that is different than the first or second polymer) to stabilize the activity of the hydrophilic bioactive agent, and/or provide another level of control of release of the hydrophilic bioactive agent from the microparticle.

The second polymer, given its hydrophobic and hydrophilic property, facilitates and modulates release of the bioactive agent from the microparticles and the matrix. In some specific aspects, the weight ratio of the second polymer to the microparticles in the matrix is in the range of 0.1:1 to 10:1, and more specifically in the range of 0.5:1 to 1:1.

The particular combination and characteristics of the first polymer, the second polymer, and microparticle comprising the hydrophilic bioactive agent provides a remarkably effective system for the controlled release of the hydrophilic bioactive agent when the elution control matrix is placed in a subject. For example, the elution control matrix of the invention can prevent a short-term burst of hydrophilic bioactive agent, which would otherwise deplete the hydrophilic bioactive agent from the matrix and compromise its therapeutic usefulness.

In more specific aspects, the microparticles comprise a hydrophilic bioactive agent that is a macromolecule. For example, the macromolecular bioactive agent can be selected from the group consisting of polypeptides, polynucleotides, and polysaccharides. Exemplary polypeptides include antibodies and antibody fragments, such as Fab fragments. In many aspects, the microparticles are composed predominantly or entirely of the hydrophilic bioactive agent, such as a Fab microparticle.

When the microparticles are composed predominantly or entirely of the hydrophilic bioactive agent, the elution control matrix can have high bioactive agent loading. For example, in some aspects, based on the microparticle load, the hydrophilic bioactive agent is present in the matrix in an amount in the range of 30% to 70% by weight solids.

Using a high loading of bioactive agent, along with the elution control that the components of the matrix provide, matrices can be fabricated so the hydrophilic bioactive agent is released from the matrix with a sustained-release profile. In this case, the sustained-release profiles of the microparticle-containing matrices of the present invention allow for release of the hydrophilic bioactive agent from an implantable medical device over a longer and more therapeutically useful time period. The elution control matrices of the present invention can be particularly useful for treatment of medical conditions that indicate a longer course of treatment. For example, in some aspects, the elution control matrix can be placed at an intravascular or intraocular location for the site-specific treatment of a medical condition over a period of a month.

The elution control matrix can be in the form of a coating, which can be present on all or a portion of an implantable medical device. The components of the present invention are amenable for forming desirable coatings on surfaces of implantable medical devices. Upon placement at a target site in the body, the hydrophilic bioactive agent can be released from the coating in a controlled manner.

In another embodiment, the invention includes a method for forming an elution control matrix. The method includes steps of providing a composition comprising a first polymer that is hydrophobic, a second polymer comprising hydrophobic and hydrophilic segments, and plurality of microparticles dispersed in the composition, wherein the microparticles comprise a hydrophilic bioactive agent. The method also includes a step of disposing the composition on the surface of a substrate. In some specific modes of practice, the method comprises spray coating the composition on a substrate to form a coating.

In another embodiment, the invention provides an elution control matrix comprising a polymeric matrix formed of at least a first polymer that is hydrophobic, and a plurality of microparticles disposed in the matrix, the microparticles comprising a hydrophilic bioactive agent and a crosslinked hydrophilic polymer. Exemplary hydrophilic polymers include natural biodegradable polysaccharides such as maltodextrin and polyalditol, which are crosslinked via pendent coupling groups. The crosslinked polymers can be in the form of a coating on a microparticle surface that encapsulates the hydrophilic bioactive agent. The crosslinked polymers can also form a crosslinked matrix throughout the microparticle.

BRIEF DESCRIPTION OF THE FIGURES

The invention may be more completely understood in connection with the following figures, in which:

FIG. 1 is a graph showing elution of active IgG from coated metal coils.

FIG. 2 is a graph showing elution of active IgG from coated metal stents.

FIG. 3 is a graph showing elution of total IgG from coated metal stents.

FIG. 4 is a graph showing elution of total IgG from coated metal coils.

FIG. 5 is a graph showing elution of total IgG from coated metal coils.

FIG. 6 is a graph showing elution of total IgG from particles.

FIG. 7 is a graph showing elution of total IgG from particles.

FIG. 8 is a graph showing elution of total Fab from coated metal coils.

FIG. 9 is a graph showing elution of total Fab from coated metal coils.

FIG. 10 is a graph showing elution of total Fab from coated metal coils.

FIG. 11 is a graph showing elution of total Fab from coated metal coils.

DETAILED DESCRIPTION OF THE INVENTION

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The present invention generally relates to a microparticle-containing polymeric matrix for the controlled release of a hydrophilic bioactive agent. Generally, the matrix is configured for placement in contact with body tissue or fluid (an "elution environment") in which the hydrophilic bioactive agent becomes released from the matrix and available to a subject. The release of the bioactive agent can be site specific, and used to treat a medical condition.

The elution control matrix can be in any one or more various forms that provide an effective vehicle for release of the bioactive agent. In some aspects, the elution control matrix is present in the form of a coating on the surface of an implantable medical device (examples are which are provided herein). It is noted that many particular compositions of the invention are suitable for forming elution control matrices in the form of coatings with desirable properties, such as strength, compliance, durability, etc.

The elution control matrix can also be in other forms. For example, the elution control matrix can be formed within a medical device, such as within an inner space (e.g., a lumen) of a device, with the device arranged so that the bioactive agent can be released through a part of the device, such as an aperture or a membrane that is associated with the device, and through which the bioactive agent can pass.

In another form, the elution control matrix can be fabricated as an implant itself. In this case, the elution control matrix is in the form of an implant, such as a filament, coil, or prosthesis. The elution control matrix in the form of an implant can serve as reservoir for release of the hydrophilic bioactive agent, or may also include some structure that (in addition to its drug releasing capability) can be placed in a subject to provide a mechanical feature.

In an embodiment, the invention includes an elution control coating with a polymeric matrix comprising a first polymer and a plurality of microparticles dispersed within the polymeric matrix. Various aspects of the invention will now be described in greater detail.

The elution control matrix can be non-degradable, partially degradable, or fully degradable. Both degradable and non-degradable polymers can be used in embodiments of the invention. In some aspects, the portions of the matrix include degradable polymers, which can facilitate and control release of the bioactive agent. In some aspects, the microparticles include degradable polymers.

The use of degradable polymers in the elution control coating can offer the advantage of controlling elution rate of a bioactive agent without depending solely on the process of the bioactive agent diffusing through the matrix itself. Rather, as portions of the matrix erodes (e.g., through bulk or surface erosion) the bioactive agent is released into the local environment of the elution control coating.

The term "degradable" as used herein with reference to polymers, shall refer to those natural or synthetic polymers that break down under physiological conditions (such as by enzymatic or non-enzymatic processes) into constituent components over a period of time. The terms "erodible", "bioerodible", "biodegradable" and "non-durable" shall be used herein interchangeably with the term "degradable".

By way of example, many degradable polymers include hydrolytically unstable linkages in the polymeric backbone. The cleavage of these hydrolytically unstable linkages leads to degradation of the polymer. Other degradable polymers (such as natural biodegradable polymers) include enzymatically cleavable linkages that can be cleaved, leading to degradation of the polymer. These polymers can be enzymatically degraded but are generally non-enzymatically hydrolytically stable. Yet other types of polymers that can be used in the elution control matrix of the invention have both enzymatically cleavable linkages and hydrolytically unstable linkages.

In some embodiments of the invention, the elution control matrix of the invention includes at least three components. One component is a hydrophobic polymer. The hydrophobic polymer can form at least part of the polymeric matrix in which the microparticles are present. Another component is a set of microparticles comprising hydrophilic bioactive agent, which can be immobilized in the matrix, and from which the hydrophilic bioactive agent can be released. Another component is a second polymer comprising hydrophobic and hydrophilic segments. In many aspects, the second polymer is included in the matrix with the first polymer.

In order to describe aspects of the invention, a method for preparing the elution control matrix from a composition comprising the first polymer, second polymer, and microparticles is described. The elution control matrix may also be prepared according to other methods, some of which are described herein.

The elution control matrices of the present invention can contain one or more bioactive agents. In the least, the microparticles present in the elution control matrix include a hydrophilic bioactive agent.

According to the invention, hydrophilic bioactive agent is provided in the form of microparticles. In the elution control matrix, the microparticles of the invention are, in essence, microdomains of hydrophilic bioactive agent. The use of hydrophilic bioactive agent in the form of microparticles is advantageous as it allows for the preparation of matrices with a desired distribution of bioactive agent in the matrix. The use of microparticles, in combination with the matrix materials described herein, is also advantageous for the controlled release of bioactive agent. As yet another advantage, the microparticulate form can preserve bioactive agent activity because, in theory, within the microparticle the bioactive agent is not subject to the same structurally altering forces as it would be if it were simply solvated in the solvent or in an emulsion with the solvent.

Microparticles used with embodiments of the invention may be configured to provide a desired bioactive agent elution rate. The rate of bioactive agent elution from a microparticle will depend on various factors including the size of the microparticle, the presence or absence of other optional components in the microparticle such as a polymer, an additive, or a solvent, the erosion characteristics of the material in the microparticle, the structural features of the microparticle including porosity, overcoats and the like.

The term "microparticle" as used herein shall refer to non-dissolved particulate matter having a size of less than 1 mm in diameter (when observed as individual, discrete microparticles). The term "microparticle" also encompasses nanoparticles. In specific aspects, the elution control matrix includes a set of microparticles having an average diameter ("dn", number average) from about 10 nm to about 100 µm. In some more specifically aspects, the elution control matrix comprises a set of microparticles is used having an average diameters from about, from about 100 nm to about 25 µm, from about 500 nm to about 15 µm, or even more specifically from about 1 µm to about 10 µm. In an embodiment, microparticles are equal to or less than about 5 µm.

In some aspects of the invention, a microparticle set having a smaller average diameter is used to prepare the elution control matrix. The use of smaller diameter microparticles may improve control over release of the hydrophilic bioactive agent, such as in terms of rate and duration of release from the matrix. The use of smaller diameter microparticles can also improve aspects of matrix formation. For example smaller microparticles can provide smoother coatings and are also less likely to clog coating equipment. In some aspects the small microparticles have a diameter of less than about 10 µm.

In many aspects, the elution control matrix includes particles that are spherical or substantially spherical in shape. In a spherical particle, distances from the center (of the microparticle) to the outer surface of the microparticle will about the same for any point on the surface of the microparticle. A substantially spherical microparticle is where there may be a difference in radii, but the difference between the smallest radii and the largest radii is generally not greater than about 40% of the smaller radii, and more typically less than about 30%, or less than 20%.

The microparticle of the invention comprises a hydrophilic bioactive agent. The hydrophilic bioactive agent can have a solubility of at least 1 part agent per 50 parts water. In more specific aspects, the hydrophilic bioactive agent may be soluble (having a solubility of at least 1 part agent per from 10 to 30 parts water), freely soluble (having a solubility of at least 1 part agent per from 1 to 10 parts water), or very soluble (having a solubility of greater than 1 part agent per 1 part water). These descriptive terms for solubility are standard terms used in the art (see, for example, *Remington: The Science and Practice of Pharmacy*, $20^{th}$ ed. (2000), Lippincott Williams & Wilkins, Baltimore Md.).

In some aspects the hydrophilic bioactive agent is a macromolecule. Hydrophilic macromolecules are exemplified by compounds such as polypeptides, polynucleotides, and polysaccharides. The hydrophilic macromolecules can have a molecular weight of about 1000 Da or greater, 5,000 Da or greater, or 10,000 Da or greater.

In some specific aspects, the microparticle comprises a polypeptide. A polypeptide refers to an oligomer or polymer including two or more amino acid residues, and is intended to encompass compounds referred to in the art as proteins, polypeptides, oligopeptides, peptides, and the like. By way of example, peptides can include antibodies (both monoclonal and polyclonal), antibody derivatives (including diabodies, F(ab) fragments, humanized antibodies, etc.), cytokines, growth factors, receptor ligands, enzymes, and the like.

Polypeptides can also include those that are modified with, or conjugated to, another biomolecule or biocompatible compound. For example, the polypeptide can be a peptide-nucleic acid (PNA) conjugate, polysaccharide-peptide conjugates (e.g., glyosylated polypeptides; glycoproteins), a poly(ethyleneglycol)-polypeptide conjugate (PEG-ylated polypeptides).

In some modes of practice, the microparticles are prepared from polypeptides having a molecular weight of about 10,000 Da or greater, or about 20,000 Da or greater; more specifically in the range of about 10,000 Da to about 100,000 Da, or in the range of about 25,000 Da to about 75,000 Da.

One class of polypeptides that can be formed into the microparticles of the invention includes antibodies and antibody fragments. A variety of antibody and antibody fragments are commercially available, obtainable by deposit or deposited samples, or can be prepared by techniques known in the art. For example, monoclonal antibodies (mAbs) can be obtained by any technique that provides for the production of antibody molecules by continuous cell lines in culture. These include, for example, the hybridoma technique (Kohler and Milstein, Nature, 256:495-497 (1975)); the human B-cell hybridoma technique (Kosbor et al., Immunology Today, 4:72 (1983); and the EBV-hybridoma technique (Cole et al., Monoclonal Antibodies and Cancer Therapy, Alan R. Liss, Inc., pp. 77-96 (1985)). Such antibodies may be of any immunoglobulin class including IgG, IgM, IgE, IgA, IgD and any subclass thereof.

Fab or Fab'2 fragments can be generated from monoclonal antibodies by standard techniques involving papain or pepsin digestion, respectively. Kits for the generation of Fab or Fab'2 fragments are commercially available from, for example, Pierce Chemical (Rockford, Ill.).

Examples of antibodies and antibody fragments that can be used to prepare the microparticles of the present invention include, but are not limited to, therapeutic antibodies include trastuzumab (Herceptin™), a humanized anti-HER2 monoclonal antibody (mAb); alemtuzumab (Campath™), a humanized anti-CD52 mAb; gemtuzumab (Mylotarg™), a humanized anti-CD33 mAb; rituximab (Rituxan™), a chimeric anti-CD20 mAb; ibritumomab (Zevalin™), a murine mAb conjugated to a beta-emitting radioisotope; tositumomab (Bexxar™), a murine anti-CD20 mAb; edrecolomab (Panorex™), a murine anti-epithelial cell adhesion molecule mAb; cetuximab (Erbitux™), a chimeric anti-EGFR mAb; bevacizumab (Avastin™), a humanized anti-VEGF mAb, Ranibizumab (Lucentis™), an anti-vascular endothelial growth factor mAb fragment, satumomab (OncoScint™) an anti-pancarcinoma antigen (Tag-72) mAb, pertuzumab (Omnitarg™) an anti-HER2 mAb, and daclizumab (Zenapax™) an anti IL-2 receptor mAb.

The polypeptide can also be selected from cell response modifiers. Cell response modifiers include chemotactic factors such as platelet-derived growth factor (PDGF), pigmented epithelium-derived factor (PEDF), neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, vascular endothelial growth factor, bone morphogenic proteins, and bone growth/cartilage-inducing factor (alpha and beta). Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin.

The polypeptide can also be selected from therapeutic enzymes, such as proteases, phospholipases, lipases, glycosidases, cholesterol esterases, and nucleases.

Specific examples include recombinant human tissue plasminogen activator (alteplase), RNaseA, RNaseU, chondroitinase, pegaspargase, arginine deaminase, vibriolysin, sarcosidase, N-acetylgalactosamine-4-sulfatase, glucocerebrocidase, α-galactosidase, and laronidase.

In many aspects of the invention, the microparticle is composed predominantly of, or entirely of, hydrophilic bioactive agent. For example, the microparticle polypeptide can include hydrophilic bioactive agent in an amount of about 90% wt or greater, about 95% wt or greater, about 98% wt or greater, or even about 99% wt or greater. This can be important in many therapeutic methods, as the amount of hydrophilic bioactive agent that is available to a subject following administration of the microparticles can be maximized.

In some preparations, the elution control matrix comprises microparticles composed predominantly of polypeptides. For example, polypeptide microparticles can be formed as described in commonly owned patent application Ser. No. 60/937,492, entitled "Polypeptide Microparticles", and filed on Jun. 28, 2007 and now U.S. patent application Ser. No. 12/215,504, and published as US 2009/0028956. Generally, these microparticles are formed in a solution, by coalescing polypeptides with a nucleating agent to form polypeptide nuclei; mixing a phase separation agent with the solution to further coalesce polypeptide around the polypeptide nuclei, thereby forming a mixture; cooling the mixture to form polypeptide microparticles; and removing all or part of the phase separation agent from the polypeptide microparticles. This method has been found to be particularly advantageous for the preparation of microparticles formed predominantly of antibody or antibody fragments, and provides microparticle sets having microparticles of desired sizes, with low size polydispersity, and which maintains good polypeptide activity.

Optionally, the microparticle can include a component that is different than the hydrophilic bioactive agent. The optional component can offer the advantage of providing additional control over the elution rate of the bioactive agent. In some embodiments, optional component can offer the advantage of increased protection of bioactive agent activity. This component can be a polymer, and can be distinct from the first and second polymer of the elution control matrix. Depending on the composition of the matrix (i.e., the number of distinct polymers that are used to form the matrix), the optional polymer can be referred to as the "third polymer," "fourth polymer," etc.

The optional polymer used with the microparticle can be degradable or non-degradable. A specific polymer can be selected based on various factors including compatibility with the bioactive agent, whether or not the polymer is degradable, speed and mode of erosion (bulk or surface), and compatibility or incompatibility with solvents used to apply the coating.

The polymer can be crosslinked in the particle, on the surface of the particle, or both. The polymer can include coupling groups, such as polymerizable groups, or reactive groups of a reactive pair (e.g., amine and amine-reactive groups) so that crosslinking can be established. A polymerization initiator can be included to promote crosslinking of polymers with polymerizable groups (macromers).

In an embodiment, the microparticle includes a degradable polymer. Elution of a bioactive agent from a particle including a degradable polymer can be from diffusion of the bioactive agent through the degradable polymer itself or through the erosion (bulk or surface erosion) of the degradable polymer. Degradable polymers can include those described in more detail below.

In some preparations, the microparticles include a natural biodegradable polysaccharide. The microparticle can be formed of a crosslinked matrix of natural biodegradable polysaccharide, with the hydrophilic bioactive agent within the crosslinked matrix. The microparticle can also have a coating or shell of crosslinked matrix of natural biodegradable polysaccharide. For example, the coating or shell can encompass a central core of bioactive agent. In this aspect, the central core can be a polypeptide microparticle as described above.

In some desired modes of practice, the biodegradable polysaccharide has a molecular weight of 500,000 Da or less, and includes pendent coupling groups (which allow for polysaccharide crosslinking). The pendent coupling groups can be in the form of polymerizable groups, or chemical groups forming a reactive pair (such as amine and amine-reactive groups). Exemplary biodegradable polysaccharides include amylose, maltodextrin, and polyalditol.

In some embodiments, the microparticles used are substantially monodisperse. In other embodiments, the microparticles used are polydisperse. In some applications, the use of substantially monodisperse microparticles is advantageous because elution rates from substantially monodisperse microparticles can be more consistent than release rates from otherwise similar polydisperse microparticles.

Microparticles having a characteristic elution rate can be combined with other microparticles having the same or a different characteristic elution rate. By combining particles with different characteristic release rates, the overall release rate of a bioactive agent from the particles and from the matrix that the particles are dispersed in can be manipulated as desired. For example, microparticles having a relatively fast elution rate can be combined in a coating with microparticles having a relatively slow elution rate to produce a composition elution profile that is desirable.

Optionally, one or more additional bioactive agents that are different than the hydrophilic bioactive agent can be present in the elution control matrix. For example, one or more additional hydrophilic bioactive agents can be present in the microparticle, such as two different polypeptides.

As another example, non-hydrophilic bioactive agents can optionally be present in the elution control matrix. For example, compounds that are poorly water soluble, or water insoluble, can be provided within the matrix formed from the first polymer. For example, such an elution control matrix can be prepared by forming a composition that includes (a) the microparticles formed from a hydrophilic bioactive agent such as a polypeptide, (b) the first polymer, (c) a second bioactive agent, and (d) an organic solvent in which both the first polymer and second bioactive agent are soluble. The second bioactive agent can diffuse directly out of the matrix formed from the first polymer to provide an additional therapeutic effect.

The hydrophilic bioactive agent, and other bioactive agents that can be optionally included in the matrix (such as a second bioactive agent), can be selected from those known in the art, including those exemplified herein.

As used herein, the term "bioactive agent" means a compound that has a particular desired biological activity. For example, a bioactive agent can be a therapeutic compound that exerts a specific activity on a subject. In some embodiments, bioactive agent will, in turn, refer to a peptide, protein, carbohydrate, nucleic acid, lipid, polysaccharide or combinations thereof, or synthetic inorganic or organic molecule, that causes a desired biological effect when administered in vivo to an animal, including but not limited to birds and mammals, including humans. Bioactive agents can have many different types of elution profiles.

Bioactive agents useful in the present invention can include many types of therapeutics including thrombin inhibitors, antithrombogenic agents, thrombolytic agents, fibrinolytic agents, anticoagulants, anti-platelet agents, vasospasm inhibitors, calcium channel blockers, steroids, vasodilators, anti-hypertensive agents, antimicrobial agents, antibiotics, antibacterial agents, antiparasite and/or antiprotozoal solutes, antiseptics, antifungals, angiogenic agents, anti-angiogenic agents, inhibitors of surface glycoprotein receptors, antimitotics, microtubule inhibitors, anti-secretory agents, actin inhibitors, remodeling inhibitors, antisense nucleotides, anti-metabolites, miotic agents, anti-proliferatives, anticancer chemotherapeutic agents, anti-neoplastic agents, anti-polymerases, anti-virals, anti-AIDS substances, anti-inflammatory steroids or non-steroidal anti-inflammatory agents, analgesics, antipyretics, immunosuppressive agents, immunomodulators, growth hormone antagonists, growth factors, radiotherapeutic agents, peptides, proteins, enzymes, extracellular matrix components, ACE inhibitors, free radical scavengers, chelators, anti-oxidants, photodynamic therapy agents, gene therapy agents, anesthetics, immunotoxins, neurotoxins, opioids, dopamine agonists, hypnotics, antihistamines, tranquilizers, anticonvulsants, muscle relaxants and anti-Parkinson substances, antispasmodics and muscle contractants, anticholinergics, ophthalmic agents, anti-glaucoma solutes, prostaglandins, antidepressants, antipsychotic substances, neurotransmitters, anti-emetics, imaging agents, specific targeting agents, and cell response modifiers.

More specifically, in embodiments the bioactive agent can include heparin, covalent heparin, synthetic heparin salts, or another thrombin inhibitor; hirudin, hirulog, argatroban, D-phenylalanyl-L-poly-L-arginyl chloromethyl ketone, or another antithrombogenic agent; urokinase, streptokinase, a tissue plasminogen activator, or another thrombolytic agent; a fibrinolytic agent; a vasospasm inhibitor; a calcium channel blocker, a nitrate, nitric oxide, a nitric oxide promoter, nitric oxide donors, dipyridamole, or another vasodilator; HYTRIN® or other antihypertensive agents; an inhibitor of surface glycoprotein receptors; aspirin, ticlopidine, clopidogrel or another antiplatelet agent; colchicine or another antimitotic, or another microtubule inhibitor; dimethyl sulfoxide (DMSO), a retinoid, or another antisecretory agent; cytochalasin or another actin inhibitor; cell cycle inhibitors; remodeling inhibitors; deoxyribonucleic acid, an antisense nucleotide, or another agent for molecular genetic intervention; an aptamer (such as MACUGEN®); methotrexate, or another antimetabolite or antiproliferative agent; tamoxifen citrate, TAXOL®, paclitaxel, or the derivatives thereof, rapamycin (or other rapalogs e.g. ABT-578 or sirolimus), vinblastine, vincristine, vinorelbine, etoposide, tenopiside, dactinomycin (actinomycin D), daunorubicin, doxorubicin, idarubicin, anthracyclines, mitoxantrone, bleomycin, plicamycin (mithramycin), mitomycin, mechlorethamine, cyclophosphamide and its analogs, chlorambucil, ethylenimines, methylmelamines, alkyl sulfonates (e.g., busulfan), nitrosoureas (carmustine, etc.), streptozocin, methotrexate (used with many indications), fluorouracil, floxuridine, cytarabine, mercaptopurine, thioguanine, pentostatin, 2-chlorodeoxyadenosine, cisplatin, carboplatin, procarbazine, hydroxyurea, morpholino phosphorodiamidate oligomer or other anti-cancer chemotherapeutic agents; cyclosporin, tacrolimus (FK-506), pimecrolimus, azathioprine, mycophenolate mofetil, mTOR inhibitors, or another immunosuppressive agent; cortisol, cortisone, dexamethasone, dexamethasone sodium phosphate, dexamethasone acetate, dexamethasone derivatives, betamethasone, fludrocortisone, prednisone, prednisolone, 6U-methylprednisolone, triamcinolone (e.g., triamcinolone acetonide), or another steroidal agent; trapidil (a PDGF antagonist), angiopeptin (a growth hormone antagonist), angiogenin, a growth factor (such as vascular endothelial growth factor (VEGF)), or another growth factor antagonist or agonist; dopamine, bromocriptine mesylate, pergolide mesylate, or another dopamine agonist; $^{60}$Co (5.3 year half life), $^{192}$Ir (73.8 days), $^{32}$P (14.3 days), $^{111}$In (68 hours), $^{90}$Y (64 hours), $^{99}$Tc (6 hours), or another radiotherapeutic agent; iodine-containing compounds, barium-containing compounds, gold, tantalum, platinum, tungsten or another heavy metal functioning as a radiopaque agent; an extracellular matrix component, a cellular component or another biologic agent; captopril, enalapril or another angiotensin converting enzyme (ACE) inhibitor; angiotensin receptor blockers; enzyme inhibitors (including growth factor signal transduction kinase inhibitors); ascorbic acid, alpha tocopherol, superoxide dismutase, deferoxamine, a 21-aminosteroid (lasaroid) or another free radical scavenger, iron chelator or antioxidant; a $^{14}$C—, $^{3}$H—, $^{131}$I—, $^{32}$P— or $^{36}$S— radiolabelled form or other radiolabelled form of any of the foregoing; an estrogen (such as estradiol, estriol, estrone, and the like) or another sex hormone; AZT or other antipolymerases; acyclovir, famciclovir, rimantadine hydrochloride, ganciclovir sodium, Norvir, Crixivan, or other antiviral agents; 5-aminolevulinic acid, meta-tetrahydroxyphenylchlorin, hexadecafluorozinc phthalocyanine, tetramethyl hematoporphyrin, rhodamine 123 or other photodynamic therapy agents; an IgG2 Kappa antibody against *Pseudomonas aeruginosa* exotoxin A and reactive with A431 epidermoid carcinoma cells, monoclonal antibody against the noradrenergic enzyme dopamine beta-hydroxylase conjugated to saporin, or other antibody targeted therapy agents; gene therapy agents; enalapril and other prodrugs; PROSCAR®, HYTRIN® or other agents for treating benign prostatic hyperplasia (BHP); VIAGRA®, mitotane, aminoglutethimide, breveldin, acetaminophen, etodalac, tolmetin, ketorolac, ibuprofen and derivatives, mefenamic acid, meclofenamic acid, piroxicam, tenoxicam, phenylbutazone, oxyphenbutazone, nabumetone, auranofin, aurothioglucose, gold sodium thiomalate, a mixture of any of these, or derivatives of any of these.

Other biologically useful compounds that can also be included in the coating include, but are not limited to, hormones, β-blockers, anti-anginal agents, cardiac inotropic agents, corticosteroids, analgesics, anti-inflammatory agents, anti-arrhythmic agents, immunosuppressants, anti-bacterial agents, anti-hypertensive agents, anti-malarials, anti-neoplastic agents, anti-protozoal agents, anti-thyroid agents, sedatives, hypnotics and neuroleptics, diuretics, anti-parkinsonian agents, gastro-intestinal agents, anti-viral agents, anti-diabetics, anti-epileptics, anti-fungal agents, histamine H-receptor antagonists, lipid regulating agents, muscle relaxants, nutritional agents such as vitamins and minerals, stimulants, nucleic acids, polypeptides, and vaccines.

Antibiotics are substances which inhibit the growth of or kill microorganisms. Antibiotics can be produced synthetically or by microorganisms. Examples of antibiotics include penicillin, tetracycline, chloramphenicol, minocycline, doxycycline, vancomycin, bacitracin, kanamycin, neomycin, gentamycin, erythromycin, geldanamycin, geldanamycin analogs, cephalosporins, or the like. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone.

Antiseptics are recognized as substances that prevent or arrest the growth or action of microorganisms, generally in a nonspecific fashion, e.g., either by inhibiting their activity or destroying them. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Antiviral agents are substances capable of destroying or suppressing the replication of viruses. Examples of anti-viral agents include α-methyl-1-adamantanemethylamine, hydroxy-ethoxymethylguanine, adamantanamine, 5-iodo-2'-deoxyuridine, trifluorothymidine, interferon, and adenine arabinoside.

Enzyme inhibitors are substances that inhibit an enzymatic reaction. Examples of enzyme inhibitors include edrophonium chloride, N-methylphysostigmine, neostigmine bromide, physostigmine sulfate, tacrine HCL, tacrine, 1-hydroxy maleate, iodotubercidin, p-bromotetramisole, 10-(α-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylaminie, N-monomethyl-L-arginine acetate, carbidopa, 3-hydroxybenzylhydrazine HCl, hydralazine HCl, clorgyline HCl, deprenyl HCl L(-), deprenyl HCl D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-di-phenylvalerate hydrochloride, 3-isobutyl-1-methylxanthne, papaverine HCl, indomethacind, 2-cyclooctyl-2-hydroxyethylamine hydrochloride, 2,3-dichloro-α-methylbenzylamine (DCMB), 8,9-dichloro-2,3,4,5-tetrahydro-1H-2-benzazepine hydrochloride, p-aminoglutethimide, p-aminoglutethimide tartrate R(+), p-aminoglutethimide tartrate S(-), 3-iodotyrosine, alpha-methyltyrosine L(-), alpha-methyltyrosine D(-), cetazolamide, dichlorphenamide, 6-hydroxy-2-benzothiazolesulfonamide, and allopurinol.

Anti-pyretics are substances capable of relieving or reducing fever. Anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances that have an anesthetic effect in a localized region. Examples of such anesthetics include procaine, lidocaine, tetracaine and dibucaine.

Imaging agents are agents capable of imaging a desired site, e.g., tumor, in vivo. Examples of imaging agents include substances having a label that is detectable in vivo, e.g., antibodies attached to fluorescent labels. The term antibody includes whole antibodies or fragments thereof.

Compounds having a steroid ring system can be referred to as steroids. In an embodiment, the bioactive agent is a steroid. Steroids include both naturally occurring compounds and synthetic analogues based on the cyclopenta[α]phenanthrene carbon skeleton, partially or completely hydrogenated. Steroids can include glucocorticoids, estrogens and androgens. By way of example, steroids can include dexamethasone, dexamethasone acetate, dexamethasone sodium phosphate, cortisone, cortisone acetate, hydrocortisone, hydrocortisone acetate, hydrocortisone cypionate, hydrocortisone sodium phosphate, hydrocortisone sodium succinate, prednisone, prednisolone, prednisolone acetate, prednisolone sodium phosphate, prednisolone tebutate, prednisolone pivalate, triamcinolone, triamcinolone acetonide, triamcinolone hexacetonide, triamcinolone diacetate, methylprednisolone, methylprednisolone acetate, methylprednisolone sodium succinate, flunsolide, beclomethasone dipropionate, betamethasone sodium phosphate, betamethasone, vetamethasone disodium phosphate, vetamethasone sodium phosphate, betamethasone acetate, betamethasone disodium phosphate, chloroprednisone acetate, corticosterone, desoxycorticosterone, desoxycorticosterone acetate, desoxycorticosterone pivalate, desoximethasone, estradiol, fluorocortisone, fluorocortisone acetate, dichlorisone acetate, fluorohydrocortisone, fluorometholone, fluprednisolone, paramethasone, paramethasone acetate, androsterone, fluoxymesterone, aldosterone, methandrostenolone, methylandrostenediol, methyl testosterone, norethandrolone, testosterone, testosterone enanthate, testosterone propionate, equilenin, equilin, estradiol benzoate, estradiol dipropionate, estriol, estrone, estrone benzoate, acetoxypregnenolone, anagestone acetate, chlormadinone acetate, flurogestone acetate, hydroxymethylprogesterone, hydroxymethylprogesterone acetate, hydroxyprogesterone, hydroxyprogesterone acetate, hydroxyprogesterone caproate, melengestrol acetate, normethisterone, pregnenolone, progesterone, ethynyl estradiol, mestranol, dimethisterone, ethisterone, ethynodiol diacetate, norethindrone, norethindrone acetate, norethisterone, fluocinolone acetonide, flurandrenolone, hydrocortisone sodium succinate, methylprednisolone sodium succinate, prednisolone phosphate sodium, triamcinolone acetonide, hydroxydione sodium, spironolactone, oxandrolone, oxymetholone, prometholone, testosterone cypionate, testosterone phenylacetate, estradiol cypionate, and norethynodrel, analogs thereof, or combinations thereof.

The elution control matrix includes a first polymer that is hydrophobic in which the microparticles are dispersed, and which provides a structural component to the matrix. Hydrophobic polymers are those having no appreciable solubility in water.

In some aspects, the hydrophobic polymer provides desirable properties when the elution control matrix is provided in certain forms. For example, when the matrix is in the form of a coating, the hydrophobic polymer can provide one or more properties of durability, compliance, etc. As used herein, the term "durability" refers to the wear resistance of a polymer coating, or the ability of a coating to adhere to an article surface when subjected to forces typically encountered during use (for example, normal force, shear force, and the like). A more durable coating is less easily removed from a substrate by abrasion. A compliant coating is one that it shapes well to the article to which is has been coated and that it can form to the changes in the shape of the article without introducing any substantial physical deformities.

In some aspects the first polymer is a durable and biostable hydrophobic polymer. Various durable and biostable hydrophobic polymer have been described in the art or are commercially available.

In some aspects the first polymer is selected from the group consisting of poly(alkyl(meth)acrylates) and poly(aromatic (meth)acrylates), where "(meth)" will be understood by those skilled in the art to include such molecules in either the acrylic and/or methacrylic form (corresponding to the acrylates and/or methacrylates, respectively).

Examples of poly(alkyl(meth)acrylates) include those with alkyl chain lengths from 2 to 8 carbons, inclusive. Exemplary sizes of poly(alkyl(meth)acrylates) are in the range of about 50 kilodaltons to about 1000 kilodaltons, about 100 kilodaltons to about 1000 kilodaltons, about 150 kilodaltons to about 500 kilodaltons, and about 200 kilodaltons to about 400 kilodaltons. One exemplary poly(alkyl(meth)acrylate is poly(n-butyl methacrylate).

Other examples of poly(alkyl(meth)acrylates) include poly (n-butyl methacrylate-co-methyl methacrylate, with a monomer ratio of 3:1, poly(n-butyl methacrylate-co-isobutyl methacrylate, with a monomer ratio of 1:1 and poly(t-butyl methacrylate). Such polymers are available commercially (e.g., from Sigma-Aldrich, Milwaukee, Wis.) with molecular weights ranging from about 150 kilodaltons to about 350 kilodaltons, and with varying inherent viscosities, solubilities and forms (e.g., as slabs, granules, beads, crystals or powder).

Examples of poly(aromatic(meth)acrylates) include poly (aryl(meth)acrylates), poly(aralkyl(meth)acrylates), poly (alkaryl(meth)acrylates), poly(aryloxyalkyl (meth)acrylates), and poly(alkoxyaryl(meth)acrylates). Specific examples of poly(aryl (meth)acrylates) include poly(9-anthracenyl methacrylate), poly(chlorophenyl acrylate), poly (methacryloxy-2-hydroxybenzophenone), poly(methacryloxybenzotriazole), poly(naphthyl acrylate), poly (naphthylmethacrylate), poly-4-nitrophenylacrylate, poly (pentachloro(bromo, fluoro) acrylate) and methacrylate, poly (phenyl acrylate) and poly(phenyl methacrylate). Specific examples of poly(aralkyl(meth)acrylates) include poly(benzyl acrylate), poly(benzyl methacrylate), poly(2-phenethyl acrylate), poly(2-phenethyl methacrylate) and poly(1-pyrenylmethyl methacrylate). Specific examples of poly(alkaryl (meth)acrylates include poly(4-sec-butylphenyl methacrylate), poly(3-ethylphenyl acrylate), and poly(2-methyl-1-naphthyl methacrylate). Specific examples of suitable poly (aryloxyalkyl (meth)acrylates) include poly(phenoxyethyl acrylate), poly(phenoxyethyl methacrylate), poly(polyethylene glycol phenyl ether acrylate) and poly(polyethylene glycol phenyl ether methacrylate) with varying polyethylene glycol molecular weights. Specific examples of poly (alkoxyaryl(meth)acrylates) include poly(4-methoxyphenyl methacrylate), poly(2-ethoxyphenyl acrylate) and poly(2-methoxynaphthyl acrylate).

Acrylate or methacrylate monomers or polymers and/or their parent alcohols are commercially available from Sigma-Aldrich (Milwaukee, Wis.) or from Polysciences, Inc, (Warrington, Pa.).

The elution control matrix can also be formed from a blend of the first polymer and another polymer that is different than the first (hydrophobic) and second (polymer comprising hydrophilic and hydrophobic segments) polymers. Depending on the composition of the matrix (i.e., the number of distinct polymers that are used to form the matrix), this polymer that can be blended with the first polymer can be referred to as the "third polymer," "fourth polymer," etc.

In some aspects the polymer that can be blended with the first polymer is poly(ethylene-co-vinyl acetate). For example, the blend can be a combination of poly(n-butyl methacrylate) (pBMA) and poly(ethylene-co-vinyl acetate) (pEVA). Such blends are described in commonly assigned U.S. Pat. No. 6,214,901 (Chudzik et al.) and US Publication No. 2002/0188037 A1 (Chudzik et al.).

In some aspects the polymer that can be blended with the first polymer is selected from the group consisting of (i) poly(alkylene-co-alkyl(meth)acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers. These blends are described in commonly assigned U.S. patent application entitled, "Coating Compositions for Bioactive Agents," U.S. Published Application 2005/0220843, filed Apr. 6, 2005.

Alternatively, these polymers can be used as the first polymer.

Poly(alkylene-co-alkyl(meth)acrylates) include those copolymers in which the alkyl groups are either linear or branched, and substituted or unsubstituted with non-interfering groups or atoms. Such alkyl groups can comprise from 1 to 8 carbon atoms, inclusive. In more specific embodiments, such alkyl groups can comprise from 1 to 4 carbon atoms, inclusive. In an embodiment, the alkyl group is methyl. In some embodiments, copolymers that include such alkyl groups can comprise from about 15% to about 80% (wt) of alkyl acrylate. When the alkyl group is methyl, the polymer contains from about 20% to about 40% methyl acrylate in some embodiments, and from about 25% to about 30% methyl acrylate in a particular embodiment. When the alkyl group is ethyl, the polymer contains from about 15% to about 40% ethyl acrylate in an embodiment, and when the alkyl group is butyl, the polymer contains from about 20% to about 40% butyl acrylate in an embodiment.

Copolymers of ethylene and other alkylenes can include straight and branched alkylenes, as well as substituted or unsubstituted alkylenes. Examples include copolymers prepared from alkylenes that comprise from 3 to 8 branched or linear carbon atoms, inclusive. In an embodiment, copolymers prepared from alkylene groups that comprise from 3 to 4 branched or linear carbon atoms, inclusive. In a particular embodiment, copolymers prepared from alkylene groups containing 3 carbon atoms (e.g., propene). By way of example, the other alkylene is a straight chain alkylene (e.g., 1-alkylene). Exemplary copolymers of this type can comprise from about 20% to about 90% (based on moles) of ethylene. In an embodiment, copolymers of this type comprise from about 35% to about 80% (mole) of ethylene. Such copolymers will have a molecular weight of between about 30 kilodaltons to about 500 kilodaltons. Exemplary copolymers are selected from the group consisting of poly(ethylene-co-propylene), poly(ethylene-co-1-butene), polyethylene-co-1-butene-co-1-hexene) and/or poly(ethylene-co-1-octene).

"Polybutenes" include polymers derived by homopolymerizing or randomly interpolymerizing isobutylene, 1-butene and/or 2-butene. The polybutene can be a homopolymer of any of the isomers or it can be a copolymer or a terpolymer of any of the monomers in any ratio. In some cases, the polybutene contains at least about 90% (wt) of isobutylene or 1-butene. In a particular embodiment, the polybutene contains at least about 90% (wt) of isobutylene. The polybutene may contain non-interfering amounts of other ingredients or additives, for example it can contain up to 1000 ppm of an antioxidant (e.g., 2,6-di-tert-butyl-methylphenol). By way of example, the polybutene can have a molecular weight between about 150 kilodaltons and about 1,000 kilodaltons. In an embodiment, the polybutene can have between about 200 kilodaltons and about 600 kilodaltons. In a particular embodiment, the polybutene can have between about 350 kilodaltons and about 500 kilodaltons. Polybutenes having a molecular weight greater than about 600 kilodaltons, including greater than 1,000 kilodaltons are available but are expected to be more difficult to work with.

Diolefin-derived, non-aromatic polymers and copolymers, including those in which the diolefin monomer used to prepare the polymer or copolymer can be derived from monomers such as butadiene ($CH_2$=CH—CH=$CH_2$) and/or isoprene ($CH_2$=CH—C($CH_3$)=$CH_2$). In an embodiment, the polymer is a homopolymer derived from diolefin monomers or is a copolymer of diolefin monomer with non-aromatic mono-olefin monomer, and optionally, the homopolymer or copolymer can be partially hydrogenated. Such polymers can be selected from the group consisting of polybutadienes prepared by the polymerization of cis-, trans- and/or 1,2-monomer units, or from a mixture of all three monomers, and polyisoprenes prepared by the polymerization of cis-1,4- and/or trans-1,4-monomer units. Alternatively, the polymer is a copolymer, including graft copolymers, and random copolymers based on a non-aromatic mono-olefin monomer such as acrylonitrile, and an alkyl (meth)acrylate and/or isobutylene. In an embodiment, when the mono-olefin monomer is acrylonitrile, the interpolymerized acrylonitrile is present at up to about 50% by weight; and when the mono-olefin monomer is isobutylene, the diolefin is isoprene (e.g., to form what is commercially known as a "butyl rubber"). Exemplary polymers and copolymers have a molecular weight between about 150 kilodaltons and about 1,000 kilodaltons. In an embodiment, polymers and copolymers have a molecular weight between about 200 kilodaltons and about 600 kilodaltons.

Additional polymers include aromatic group-containing copolymers, including random copolymers, block copolymers and graft copolymers. In an embodiment, the aromatic group is incorporated into the copolymer via the polymerization of styrene. In a particular embodiment, the random copolymer is a copolymer derived from copolymerization of styrene monomer and one or more monomers selected from butadiene, isoprene, acrylonitrile, a $C_1$-$C_4$ alkyl (meth)acrylate (e.g., methyl methacrylate) and/or butene. Useful block copolymers include copolymer containing (a) blocks of polystyrene, (b) blocks of an polyolefin selected from polybutadiene, polyisoprene and/or polybutene (e.g., isobutylene), and (c) optionally a third monomer (e.g., ethylene) copolymerized in the polyolefin block. The aromatic group-containing copolymers contain about 10% to about 50% (wt.) of polymerized aromatic monomer and the molecular weight of the copolymer is from about 300 kilodaltons to about 500 kilodaltons. In an embodiment, the molecular weight of the copolymer is from about 100 kilodaltons to about 300 kilodaltons.

Additional polymers include epichlorohydrin homopolymers and poly(epichlorohydrin-co-alkylene oxide) copolymers. In an embodiment, in the case of the copolymer, the copolymerized alkylene oxide is ethylene oxide. By way of example, epichlorohydrin content of the epichlorohydrin-containing polymer is from about 30% to 100% (wt). In an embodiment, epichlorohydrin content is from about 50% to 100% (wt). In an embodiment, the epichlorohydrin-containing polymers have a molecular weight from about 100 kilodaltons to about 300 kilodaltons.

As another example, the first polymer can be a styrene copolymer, such as poly(styrene-isobutylene-styrene); see, for example, U.S. Pat. No. 6,669,980.

Degradable polymers can also be used as the first polymer. Examples of degradable polymers can include those with hydrolytically unstable linkages in the polymeric backbone. Degradable polymers of the invention include both those with bulk erosion characteristics and those with surface erosion characteristics.

Synthetic degradable polymers can include: degradable polyesters (such as poly(glycolic acid), poly(lactic acid), poly(lactic-co-glycolic acid), poly(dioxanone), polylactones (e.g., poly(caprolactone)), poly(3-hydroxybutyrate), poly(3- hydroxyvalerate), poly(valerolactone), poly(tartronic acid), poly(β-malonic acid), poly(propylene fumarate)); degradable polyesteramides; degradable polyanhydrides (such as poly(sebacic acid), poly(1,6-bis(carboxyphenoxy)hexane, poly(1,3-bis(carboxyphenoxy)propane); degradable polycarbonates (such as tyrosine-based polycarbonates); degradable polyiminocarbonates; degradable polyarylates (such as tyrosine-based polyarylates); degradable polyorthoesters; degradable polyurethanes; degradable polyphosphazenes; and degradable polyhydroxyalkanoates; and copolymers thereof.

Naturally-based degradable polymers can include modified polysaccharides such as modified starch, cellulose, chitin, chitosan, and copolymers thereof, the modifications providing adequate solubility in a solvent-based composition used for matrix formation.

Specific examples of degradable polymers include poly (ether ester) multiblock copolymers based on poly(ethylene glycol) (PEG) and poly(butylene terephthalate) (PBT) that can be described by the following general structure:

[—(OCH$_2$CH$_2$)$_n$—O—C(O)—C$_6$H$_4$—C(O)—]$_x$[—O—(CH$_2$)$_4$—O—C(O)—C$_6$H$_4$—C(O)—]$_y$, where —C$_6$H$_4$— designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer. n can be selected such that the molecular weight of the PEG block is between about 300 and about 4000. X and y can be selected so that the multiblock copolymer contains from about 55% up to about 80% PEG by weight. The block copolymer can be engineered to provide a wide array of physical characteristics (e.g., hydrophilicity, adherence, strength, malleability, degradability, durability, flexibility) and bioactive agent release characteristics (e.g., through controlled polymer degradation and swelling) by varying the values of n, x and y in the copolymer structure.

Degradable polyesteramide polymers used in embodiments of the invention can include those having the formula [—O—(CH$_2$)$_x$—O—C(O)—CHR—NH—C(O)—(CH$_2$)$_y$—C(O)—NH—CHR—C(O)—] wherein x is C$_2$-C$_{12}$, y is C$_2$-C$_{12}$, and R is CH(CH$_3$)$_2$, CH$_2$CH(CH$_3$)$_2$, CH(CH$_3$)CH$_2$CH$_3$, (CH$_2$)$_3$CH$_3$, CH$_2$C$_6$H$_5$, or (CH$_2$)$_3$SCH$_3$. Such polymers are described in U.S. Pat. No. 6,703,040. Polymers of this nature can be described with a nomenclature of x-aa-y, wherein x represents an alkyl diol with x carbon atoms, "aa" represents an amino acid such as leucine or phenylalanine, and y represents an alkyldicarboxylic acid with y carbon atoms, and wherein the polymer is a polymerization of the diol, the dicarboxylic acid, and the amino acid. An exemplary polymer of this type is 4-Leu-4.

Degradable polymeric materials can also be selected from: (a) non-peptide polyamino polymers; (b) polyiminocarbonates; (c) amino acid-derived polycarbonates and polyarylates; and (d) poly(alkylene oxide) polymers.

In an embodiment, the degradable polymeric material is composed of a non-peptide polyamino acid polymer. Suitable non-peptide polyamino acid polymers are described, for example, in U.S. Pat. No. 4,638,045 ("Non-Peptide Polyamino Acid Bioerodible Polymers," Jan. 20, 1987). Generally speaking, these polymeric materials are derived from monomers, including two or three amino acid units having one of the following two structures illustrated below:

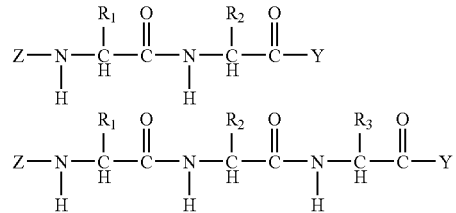

wherein the monomer units are joined via hydrolytically labile bonds at not less than one of the side groups $R_1$, $R_2$, and $R_3$, and where $R_1$, $R_2$, $R_3$ are the side chains of naturally occurring amino acids; Z is any desirable amine protecting group or hydrogen; and Y is any desirable carboxyl protecting group or hydroxyl. Each monomer unit comprises naturally occurring amino acids that are then polymerized as monomer units via linkages other than by the amide or "peptide" bond. The monomer units can be composed of two or three amino acids united through a peptide bond and thus comprise dipeptides or tripeptides. Regardless of the precise composition of the monomer unit, all are polymerized by hydrolytically labile bonds via their respective side chains rather than via the amino and carboxyl groups forming the amide bond typical of polypeptide chains. Such polymer compositions are non-toxic, are degradable, and can provide desirable release kinetics for the delivery of bioactive agents in a variety of therapeutic applications. According to these aspects, the amino acids are selected from naturally occurring L-alpha amino acids, including alanine, valine, leucine, isoleucine, proline, serine, threonine, aspartic acid, glutamic acid, asparagine, glutamine, lysine, hydroxylysine, arginine, hydroxyproline, methionine, cysteine, cystine, phenylalanine, tyrosine, tryptophan, histidine, citrulline, ornithine, lanthionine, hypoglycin A, β-alanine, γ-amino butyric acid, alpha aminoadipic acid, canavanine, venkolic acid, thiolhistidine, ergothionine, dihydroxyphenylalanine, and other amino acids well recognized and characterized in protein chemistry.

In an embodiment, the degradable polymeric material can be composed of polyiminocarbonates. Polyiminocarbonates are structurally related to polycarbonates, wherein imino groups (C=NH) are present in the places normally occupied by carbonyl oxygen in the polycarbonates. Thus, the degradable component can be formed of polyiminocarbonates having linkages

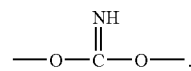

For example, one useful polyiminocarbonate has the general polymer structural formula

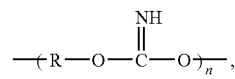

wherein R is an organic divalent group containing a non-fused aromatic organic ring, and n is greater than 1. Embodiments of the R group within the general formula above are exemplified by, but are not limited to the following:

R group (a)

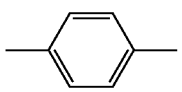

(b)

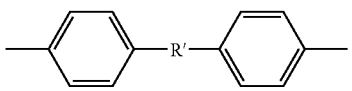

wherein R' is lower alkene $C_1$ to $C_6$ (c)

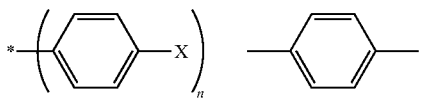

wherein n is an integer equal to or greater than 1, X is a hetero atom such as —O—, —S—, or a bridging group such as —NH—, —S(=O)—, —SO$_2$—, —C(=O)—, —C(CH$_3$)$_2$—, —CH(CH$_3$)—, —CH(CH$_3$)—CH$_2$—CH(CH$_3$)—, (d)

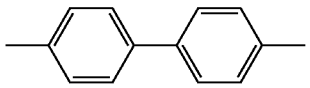

Also, compounds of the general formula

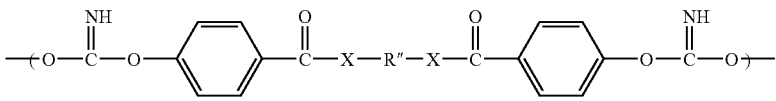

can be utilized, wherein X is O, NH, or NR''', wherein R''' is a lower alkyl radical; and R'' is a divalent residue of a hydrocarbon including polymers such as a polyolefin, an oligoglycol or polyglycol such as polyalkylene glycol ether, a polyester, a polyurea, a polyamine, a polyurethane, or a polyamide. Exemplary starting material for use in accordance with these embodiments include diphenol compounds having the formula

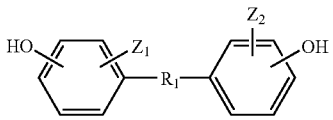

and dicyanate compounds having the formula

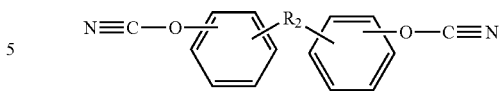

with $R_1$ and $R_2$ being the same or different and being alkylene, arylene, alkylarylene or a functional group containing heteroatoms. $Z_1$, and $Z_2$ can each represent one or more of the same or different radicals selected from the group consisting of hydrogen, halogen, lower-alkyl, carboxyl, amino, nitro, thioether, sulfoxide, and sulfonyl. Each of $Z_1$ and $Z_2$ can be hydrogen.

In an embodiment, the degradable polymeric material can be composed of various types of amino acid-derived polycarbonates and polyarylates. These amino acid-derived polycarbonates and polyarylates can be prepared by reacting certain amino acid-derived diphenol starting materials with either phosgene or dicarboxylic acids, respectively. The monomers according to this embodiment are diphenol compounds that are amino acid ester derivatives having the formula shown below:

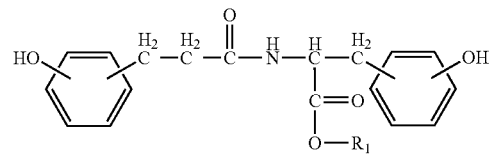

in which $R_1$ is an alkyl group containing up to 18 carbon atoms.

In yet another embodiment, the degradable polymer can be composed of copolymers containing both hydrophilic poly (alkylene oxides) (PAO) and degradable sequences, wherein the hydrocarbon portion of each PAO unit contains from 1 to 4 carbon atoms, or 2 carbon atoms (i.e., the PAO is poly (ethylene oxide)). For example, useful degradable polymeric materials can be made of block copolymers containing PAO and amino acids or peptide sequences and contain one or more recurring structural units independently represented by the structure -L-$R_1$-L-$R_2$—, wherein $R_1$ is a poly(alkylene oxide), L is —O— or —NH—, and $R_2$ is an amino acid or peptide sequence containing two carboxylic acid groups and at least one pendent amino group.

Other useful degradable polymeric materials are composed of polyarylate or polycarbonate random block copolymers that include tyrosine-derived diphenol monomers and poly (alkylene oxide), such as the polycarbonate shown below:

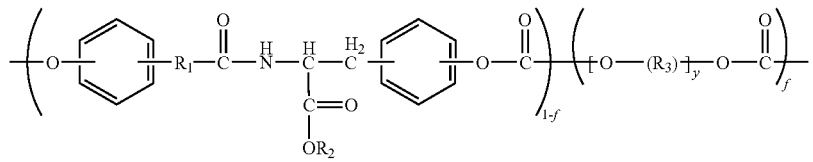

wherein $R_1$ is —CH=CH— or (—CH$_2$—)$_j$, in which j is 0 to 8; $R_2$ is selected from straight and branched alkyl and alkylaryl groups containing up to 18 carbon atoms and optionally containing at least one ether linkage, and derivatives of biologically and pharmaceutically active compounds covalently bonded to the copolymer; each $R_3$ is independently selected from alkylene groups containing 1 to 4 carbon atoms; y is between 5 and about 3000; and f is the percent molar fraction of alkylene oxide in the copolymer and ranges from about 0.01 to about 0.99.

In some embodiments, pendent carboxylic acid groups can be incorporated within the polymer bulk for polycarbonates, polyarylates, and/or poly(alkylene oxide) block copolymers thereof, to further control the rate of polymer backbone degradation and resorption.

Degradable polymers of the invention can also include polymerized polysaccharides such as those described in U.S. Patent Publication No. 2005/0255142, entitled "Coatings for Medical Articles Including Natural Degradable Polysaccharides," U.S. Patent Publication No. 2007/0065481, entitled "Coatings Including Natural Degradable Polysaccharides and Uses Thereof," and in U.S. application Ser. No. 11/724,553, entitled "Hydrophobic Derivatives of Natural Degradable Polysaccharides."

Degradable polymers of the invention can also include dextran based polymers such as those described in U.S. Pat. No. 6,303,148, entitled "Process for the Preparation of a Controlled Release System." Exemplary dextran based degradable polymers including those available commercially under the tradename OCTODEX™.

In some aspects of the invention, the elution control matrix includes a second polymer that comprises hydrophilic and hydrophobic portions. It has been found that, in association with the matrix elution control matrix, the second polymer facilitates and modulates release of the bioactive agent from the microparticles and the matrix. In some regards, the improvement in bioactive agent release may at least in part be due to the second polymer enhancing the stability of the suspension of microparticles during the process of matrix formation.

In some aspects the second polymer is a block copolymer comprising hydrophilic and hydrophobic blocks. The linkages between the blocks can be biodegradable or biostable. The hydrophilic and hydrophobic blocks can be either or both biodegradable or biostable.

Exemplary hydrophilic blocks can be selected from polymer segments formed from monomers such as ethylene glycol, ethylene oxide, vinyl alcohol, propylene oxide, vinyl pyrrolidone, hydroxy ethyl methacrylate, and hydroxy ethyl acrylate.

Exemplary hydrophilic blocks include (PEO), polyvinyl alcohol (PVA), poly(vinyl pyrrolidone) (PVP), polyacrylamide, poly(hydroxy alkyl methacrylate), poly(hydroxy ethyl methacrylate), hydrophilic polyurethane, HYPAN, oriented HYPAN, poly(hydroxy ethyl acrylate), poly(ethyloxazoline), and polyamines (e.g., Jeffamine™).

In some aspects the second polymer comprises a polyalkoxyalkane block. Representative examples of polyalkoxyalkane blocks include polyethylene glycol), tetraethylene glycol, triethylene glycol, trimethylolpropane ethoxylate, and pentaeerythritol etholxylate blocks.

Exemplary hydrophilic blocks have a molecular weight of about 100 Da to about 5000 Da, or about 250 Da to about 3500.

In some aspects the hydrophobic blocks include a biodegradable polymeric segment selected from polycaprolactone (PCL), polyvalerolactone (PVL), poly(lactide-co-glycolide) (PLGA), polylactic acid (PLA), polybutyrolactone (PBL), polyglycolide, polypropiolactone (PPL), and polytrimethylene carbonate.

In some aspects the hydrophobic block comprises a poly (alkylene dicarboxylate), such as poly(ethylene terephthalate), poly(butylene terephthalate), poly(butylene-2,6-naphthalate), poly(ethylene-2,6-naphthalate), poly (cyclohexanedimethanol terephthalate), poly(ethylene-co-cyclohexanedimethanol terephthalate), polytrimethylene terephthalate, poly(dimethanol-1,4-cyclohexanedicarboxylate), and polyxylene terephthalate.

Biodegradable polyetherester copolymers can be used as the second polymer. Generally speaking, the polyetherester copolymers are amphiphilic block copolymers that include hydrophilic (for example, a polyalkylene glycol, such as polyethylene glycol) and hydrophobic blocks (for example, polyethylene terephthalate). Specific examples of degradable polymers include poly(ether ester) multiblock copolymers based on poly(ethylene glycol) (PEG) and poly(butylene terephthalate) (PBT) that can be described by the following general structure:

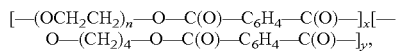

where —C$_6$H$_4$— designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer. The subscript n can be selected such that the molecular weight of the PEG block is between about 300 and about 4000. X and y can be selected so that the multiblock copolymer contains from about 55% up to about 80% PEG by weight.

The block copolymer can be engineered to provide a wide array of physical characteristics (e.g., hydrophilicity, adherence, strength, malleability, degradability, durability, flexibility) and bioactive agent release characteristics (e.g., through controlled polymer degradation and swelling) by varying the values of n, x and y in the copolymer structure. Examples of these types of multiblock copolymers are described in, for example, U.S. Pat. No. 5,980,948. PEG/PBT polymers are commercially available from Octoplus BV, under the trade designation PolyActive™.

In some aspects the second polymer comprises a hydrophilic backbone and pendent hydrophobic groups. In some aspects the hydrophilic backbone comprises a polysaccharide. Exemplary polysaccharides with pendent hydrophobic groups include fatty acid derivatized poly-α(1→4)glucopyranose polymers, such as described in U.S. patent application Ser. No. 11/724,553, filed Mar. 15, 2007 (Chudzik), and published as U.S. 2007/0260054. The polysaccharides can include a level of derivation and pendent hydrophobic groups suitable for use as a second polymer. The linkages between the hydrophilic backbone and the pendent hydrophobic groups can be hydrolytically cleavable and can include ester groups.

The hydrophilic and hydrophobic portions of the second polymer can also be defined in terms of their weight ratios in the polymer. For example, in some aspects, the weight ratio of the hydrophilic portion to the hydrophobic portions can be in the range of about 5:1 to about 1:5, about 3:1 to about 1:3, about 2:1 to about 1:2, or about 1.5:1 to about 1:1.5. For example a (poly(butyleneterephthalate-co-ethylene glycol) copolymer with 45 wt. % polyethylene glycol (having an average molecular weight of 1000 kD) and 55 wt. % butyleneterephthalate, would have a weight ratio of hydrophilic portion to hydrophobic portion of about 1:1.22.

In an embodiment, the invention includes a method for forming an elution control matrix. The method includes preparing a composition comprising plurality of microparticles and at least the first polymer, wherein the microparticles are dispersed in the composition. In some specific aspects, the composition includes the plurality of microparticles, the first polymer, and a second polymer. The coating composition is then used to form the elution control matrix. For example, the composition can be applied to a substrate to form a coating, which is the elution control matrix.

The microparticles that are used in the composition can be formed in accordance with many different techniques, including those described or referred to herein, and known to those of skill in the art. The microparticles can be provided to the composition in dry (e.g., lyophilized form) or alternatively can be provided in a solvent used in the microparticle formation process. For example, it is noted that solvents useful for extraction of phase separation agents in the microparticle formation process can also be useful as solvents during the matrix formation (e.g., coating) process.

The components of the coating composition can be added to the solvent in any particular order, or can be combined all at once. In many modes of practice the components are added with agitation to keep the microparticles dispersed.

In some modes of preparation, once the microparticles are produced or obtained, they are mixed with (a) a solvent and (b) at least the first polymer that will form the matrix ("matrix polymer"). An appropriate solvent, or solvent system, can be chosen for preparation of the composition. Different types of solvents can be used depending on the properties of the particles and the properties of the matrix polymer. Suitable solvents include those that do not cause substantial or any dissolution of the microparticles during the process. Examples of solvents include toluene and xylene, ethers such as tetrahydrofuran; and amides such as dimethylformamide (DMF). Preferred solvents for use with polypeptide microparticles include halogenated alkanes such as methylene chloride and chloroform. Combinations of one or more of these or other solvents can also be used.

During matrix formation, such as exemplified by a coating process, the composition (with the solids of the composition represented by the first polymer, microparticles, etc.) can be applied to a substrate, and then the solvent is allowed to evaporate from the surface. In some modes of practice, the composition may be prepared with the components (microparticles and polymer) at a low concentration, and the composition may be repeatedly applied to the surface build up the coating and increase the amount of solids. In some modes of practice, the composition may be prepared with the components (microparticles and polymer) at a higher concentration, and the composition applied once, or only a few times, to provide a coating with a desired amount of solids. As such, the method of forming the matrix can be quite variable, and suited to provide a coating with desired characteristics, such as amount of bioactive agent, thickness, etc.

The amount of microparticles incorporated into the matrix can be chosen based on various factors, including the type and amount of hydrophilic bioactive agent intended to be incorporated into the matrix, and the desired release rate and duration of release of the bioactive agent from the matrix.

There is no particular lower limit of amount of microparticles to be dispersed in the composition. However, exemplary concentrations of microparticles dispersed in the solvent can be up to about 25 mg/mL, such as in the range of about 5 mg/mL to about 25 mg/mL, or more specifically in the range of about 10 mg/mL to about 15 mg/mL.

The polymer components of the matrix can be added to the composition to provide a concentration of suitable for forming and holding the microparticles in place after the matrix forms, and providing a matrix with desired elution properties. The total polymer content can be at least the first polymer; the first and second polymers; or the first, second, and any additional polymers.

Exemplary concentrations of the total polymer content in the solvent can be in the range of up to 25 mg/mL such as in the range of about 10 mg/mL to about 25 mg/mL, or more specifically in the range of about 10 mg/mL to about 20 mg/mL.

In some aspects the composition comprises a first polymer and at least one other polymer that is blendable with the first polymer, but different than the second polymer. In one exemplary combination, the first polymer is a poly(alkyl(meth)acrylate), such as poly(n-butyl methacrylate), and the blendable polymer is poly(ethylene-co-vinyl acetate). As an example, the polymers can be provided in a blend wherein the ratio of the first polymer (e.g., pBMA) to the blendable polymer (e.g., pEVA) is in the range of about 10:1 to about 10:1, about 4:1 to about 1:4, or more specifically in the range of about 1:1 to about 1:4.

In some aspects the composition is prepared including the second polymer that has hydrophilic and hydrophobic portions, such as a poly(ethylene glycol)-based block copolymer. Exemplary concentrations of second polymer in the solvent can be in the range of up to 20 mg/mL, such as in the range of about 1 mg/mL to about 20 mg/mL.

After all the components of the coating solution have been combined, the matrix forming composition is processed to produce a suspension that is substantially homogenous. Depending on the nature of the composition components, this may be done using a sonication apparatus, homogenizer, stirring apparatus, or the like. In some instances, the composition forms a suspension that is stable over a period of time of about five minutes to about twenty-four hours. In other instances, the composition is not stable and must be stirred or otherwise agitated to maintain the homogeneity of the suspension. In some embodiments, other agents may be added to the suspension. By way of example, antiflocculation agents may be added.

In some aspects the matrix-forming composition is used to form a coating on a substrate. The coating composition is then applied onto the substrate using any of a variety of coating techniques including dip-coating, spray-coating (including both gas-atomization and ultrasonic atomization), fogging, brush coating, press coating, blade coating, and the like. The coating composition may be applied under conditions where atmospheric characteristics such as relative humidity, temperature, gaseous composition, and the like are controlled.

In some embodiments, the coating solution is applied using a spray technique. Exemplary spray coating equipment that can be used to apply coatings of the invention can be found in U.S. Pat. Nos. 6,562,136; 7,077,910; 7,192,484; 7,125,577; U.S. Published Patent Applications 2006/0088653, and 2005/019424; and U.S. application Ser. Nos. 11/102,465 (published as U.S. 2005/0196424) and 60/736,995.

The spray technique can be performed by spraying the composition on the surface of a substrate. Generally, an amount of solvent will evaporate during spray coating and after the composition has been applied to the surface. The composition can be repeatedly sprayed on the surface to provide a coating with desired properties, such as thickness and amount of bioactive agent per unit area on the surface. The coating evaporates from the applied composition, leaving a coating of solids on the surface. The process can be carried out to provide the coating with desired features The coating can have certain dimensions, such as thickness. In many aspects the thickness will be relatively uniform over the entire coating on the surface. A coating process can be carried out to provide a coating that is at least based on the size of the microparticles that are included in the coating. In many aspects, the thickness of the coating is greater than the diameter of the microparticles present in the coating. For example, the thickness of the coating can be greater than about 5 µm, greater than about 10 µm. Exemplary coatings have thicknesses in the range of about 40 µm to about 50 µm.

In other modes of practice, the coating process is carried out wherein components used to form the coating are separately sprayed on the substrate, using two or more sprayed solutions. For example, the coating process can be carried out using a spray coating apparatus with a dual spray head as described in U.S. Published Patent Application No, 2007/0128343, entitled "Apparatus and Methods for Applying Coatings." To exemplify this method, one composition including the first polymer and microparticles is sprayed from a first spray head, and another composition including the second polymer is sprayed from a second spray head. The spray patterns from both spray heads are directed at the same location on the surface of the substrate, and the components can mix during the coating process to form the coating.

Other types of processes can be used to form an elution control matrix. As previously mentioned, the matrix can be in the form of a mass within an implantable article, such as a lumen of an implantable article. The composition can be disposed in the lumen, with the removal of solvent during the process, to form a matrix within the lumen of the article. Following formation and implantation, the matrix can be contacted with a body fluid through a portion of the article, such as an aperture, which causes the bioactive agent to be eluted from the matrix through the aperture.

In another mode of practice, the elution control matrix is prepared in the form of an implant, which is composed of the matrix itself. The implant can be in the form of a filament, coil, or prosthesis, such that when the implant is placed in a subject, the bioactive agent can be released from the matrix. In one mode of preparation, the implant is formed by disposing the composition in a mold, and then, following solvent removal and solidification of the matrix, removing the formed implant from the mold.

The elution control matrix can also be discussed in terms of the amounts of the components of the matrix (at particular percentages by weight solids), or amounts of components in the formed matrix, in relation to one another.

In some aspects, the elution control matrix has an amount of microparticles (i.e., the amount of microparticles as a percentage of the total weight of the coating) of up to about 70% wt, in the range of about 30% wt to about 60% wt, about 30% wt to about 50% wt, or about 30% wt to about 40% wt.

In some aspects, the elution control matrix has an amount of total polymeric content (i.e., the amount of first polymer, second polymer, and any additional polymer as a percentage of the total weight of the elution control matrix) of greater than 30% wt, in the range of about 30% wt to about 70% wt, about 40% wt to about 70% wt, about 50% wt to about 70% wt, or about 60% wt to about 70% wt.

In some aspects, the elution control matrix has an amount of first polymer (or combination of all polymeric material minus the second polymer) in the range of about 30% wt to about 70% wt, about 30% wt to about 60% wt, or about 30% wt to about 50% wt.

In some aspects, the elution control matrix has an amount of second polymer in the range of about 1% wt to about 30% wt, about 5% wt to about 25% wt, or about 10% wt to about 20% wt.

In some aspects, the weight ratio of the second polymer to the first polymer (or the ratio of the second polymer to the combination of all other polymers in the matrix (with the exception of the microparticles)) is in the range of about 1:1 to about 1:10.

In some aspects, the weight ratio of the second polymer to the microparticles in the matrix is in the range of about 0.1:1 to about 1:10, or about 0.5:1 to about 1:1.

In exemplary preparations, the matrix comprises microparticles at about 30 wt %, second polymer at about 15 wt %, and remaining polymeric material (i.e., the first polymer and any other matrix-forming polymer) at about 55 wt %.

Embodiments of the invention can be used to form elution control matrices in association with many different types of devices, including medical devices, including many different types of substrates. Medical devices can include both implantable devices (chronically and transiently implantable) and non-implantable medical devices. In many aspects, a composition used to form the elution control matrix can be formed into a device as described herein.

Embodiments of the invention can be used with implantable, or transitorily implantable, devices including, but not limited to, vascular devices such as grafts (e.g., abdominal aortic aneurysm grafts, etc.), stents (e.g., self-expanding stents typically made from nitinol, balloon-expanded stents typically prepared from stainless steel, degradable coronary stents, etc.), catheters (including arterial, intravenous, blood pressure, stent graft, etc.), valves (e.g., polymeric or carbon mechanical valves, tissue valves, valve designs including percutaneous, sewing cuff, and the like), embolic protection filters (including distal protection devices), vena cava filters, aneurysm exclusion devices, artificial hearts, cardiac jackets, and heart assist devices (including left ventricle assist devices), implantable defibrillators, electro-stimulation devices and leads (including pacemakers, lead adapters and lead connectors), implanted medical device power supplies (e.g., batteries, etc.), peripheral cardiovascular devices, atrial septal defect closures, left atrial appendage filters, valve annuloplasty devices (e.g., annuloplasty rings), mitral valve repair devices, vascular intervention devices, ventricular assist pumps, and vascular access devices (including parenteral feeding catheters, vascular access ports, central venous access catheters); surgical devices such as sutures of all types, staples, anastomosis devices (including anastomotic closures), suture anchors, hemostatic barriers, screws, plates, clips, vascular implants, tissue scaffolds, cerebra-spinal fluid shunts, shunts for hydrocephalus, drainage tubes, catheters including thoracic cavity suction drainage catheters, abscess drainage catheters, biliary drainage products, and implantable pumps; orthopedic devices such as joint implants, acetabular cups, patellar buttons, bone repair/augmentation devices, spinal devices (e.g., vertebral disks and the like), bone pins, cartilage repair devices, and artificial tendons; dental devices such as dental implants and dental fracture repair devices; drug delivery devices such as drug delivery pumps, implanted drug infusion tubes, drug infusion catheters, and intravitreal drug delivery devices; ophthalmic devices including orbital implants, glaucoma drain shunts and intraocular lenses; urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices; synthetic prostheses such as breast prostheses and artificial organs (e.g., pancreas, liver, lungs, heart, etc.); respiratory devices including lung catheters; neurological devices such as neurostimulators, neurological catheters, neurovascular balloon catheters, neuro-aneurysm treatment coils, and neuropatches; ear nose and throat devices such as nasal buttons, nasal and airway splints, nasal tampons, ear wicks, ear drainage tubes, tympanostomy vent tubes, otological strips, laryngectomy tubes, esophageal tubes, esophageal stents, laryngeal stents, salivary bypass tubes, and tracheostomy tubes; biosensor devices including glucose sensors, cardiac sensors, intra-arterial blood gas sensors; oncological implants; and pain management implants.

Classes of suitable non-implantable devices can include dialysis devices and associated tubing, catheters, membranes, and grafts; autotransfusion devices; vascular and surgical devices including atherectomy catheters, angiographic catheters, intraaortic balloon pumps, intracardiac suction devices, blood pumps, blood oxygenator devices (including tubing and membranes), blood filters, blood temperature monitors, hemoperfusion units, plasmapheresis units, transition sheaths, dialators, intrauterine pressure devices, clot extraction catheters, percutaneous transluminal angioplasty catheters, electrophysiology catheters, breathing circuit connectors, stylets (vascular and non-vascular), coronary guide wires, peripheral guide wires; dialators (e.g., urinary, etc.); surgical instruments (e.g. scalpels and the like); endoscopic devices (such as endoscopic surgical tissue extractors, esophageal stethoscopes); and general medical and medically related devices including blood storage bags, umbilical tape, membranes, gloves, surgical drapes, wound dressings, wound management devices, needles, percutaneous closure devices, transducer protectors, pessary, uterine bleeding patches, PAP brushes, clamps (including bulldog clamps), cannulae, cell culture devices, materials for in vitro diagnostics, chromatographic support materials, infection control devices, colostomy bag attachment devices, birth control devices; disposable temperature probes; and pledgets.

In some aspects, embodiments of the invention can be utilized in connection with ophthalmic devices. Suitable ophthalmic devices in accordance with these aspects can provide bioactive agent to any desired area of the eye. In some aspects, the devices can be utilized to deliver bioactive agent to an anterior segment of the eye (in front of the lens), and/or a posterior segment of the eye (behind the lens). Suitable ophthalmic devices can also be utilized to provide bioactive agent to tissues in proximity to the eye, when desired.

In some aspects, embodiments of the invention can be utilized in connection with an ophthalmic device configured for placement at an external or internal site of the eye. Suitable external devices can be configured for topical administration of bioactive agent. Such external devices can reside on an external surface of the eye, such as the cornea (for example, contact lenses) or bulbar conjunctiva. In some embodiments, suitable external devices can reside in proximity to an external surface of the eye.

Devices configured for placement at an internal site of the eye can reside within any desired area of the eye. In some aspects, the ophthalmic devices can be configured for placement at an intraocular site, such as the vitreous. Illustrative intraocular devices include, but are not limited to, those described in U.S. Pat. Nos. 6,719,750 B2 ("Devices for Intraocular Drug Delivery," Varner et al.) and 5,466,233 ("Tack for Intraocular Drug Delivery and Method for Inserting and Removing Same," Weiner et al.); U.S. Patent Publication Nos. 2005/0019371 A1 ("Controlled Release Bioactive Agent Delivery Device," Anderson et al.), 2004/0133155 A1 ("Devices for Intraocular Drug Delivery," Varner et al.), 2005/0059956 A1 ("Devices for Intraocular Drug Delivery," Varner et al.), and 2003/0014036 A1 ("Reservoir Device for Intraocular Drug Delivery," Varner et al.); and U.S. Patent Publication Nos. 2005/0276837 A1 (filed Dec. 15, 2005, Anderson et al.), 2004/0271706 A1 (filed Dec. 8, 2005, Anderson et al.), 20050287188 A1 (filed Dec. 29, 2005, Anderson et al.), 2008/0271703 A1 (filed Dec. 8, 2005, Anderson et al.), 2005/0281863 A1 (filed Dec. 22, 2005, Anderson et al.); and related applications.

In some aspects, the ophthalmic devices can be configured for placement at a subretinal area within the eye. Illustrative ophthalmic devices for subretinal application include, but are not limited to, those described in U.S. Patent Publication No. 2005/0143363 ("Method for Subretinal Administration of Therapeutics Including Steroids; Method for Localizing Pharmacodynamic Action at the Choroid and the Retina; and Related Methods for Treatment and/or Prevention of Retinal Diseases," de Juan et al.); U.S. Patent Publication No. 2006/0110428, filed Jul. 5, 2005, ("Methods and Devices for the Treatment of Ocular Conditions," de Juan et al.); and related applications.

Suitable ophthalmic devices can be configured for placement within any desired tissues of the eye. For example, ophthalmic devices can be configured for placement at a subconjunctival area of the eye, such as devices positioned extrasclerally but under the conjunctiva, such as glaucoma drainage devices and the like.

The present invention may be better understood with reference to the following examples. These examples are intended to be representative of specific embodiments of the invention, and are not intended as limiting the scope of the invention.

Measurements of protein (Fab fragment) concentration, as eluted from the polymeric matrices of the example, was determined spectrophotometrically by measuring absorbance at about 280 nm ($A_{280}$). Light of this wavelength is absorbed by aromatic amino acids, and most intensely by tryptophan. Calibration samples of Fab fragment were prepared at concentrations 250, 125, 62.5, 31.3, 15.6, and 7.8 µg/mL for preparation of a standard plot. Aliquots of 150 µL of the calibration samples (in triplicate) and 150 µL of elution samples (in duplicate) were pipetted into a black 96-well plate. To all samples 150 µL of a 12 M guanidine-HCl solution in deionized distilled water (DDW) was added. The plate was placed in a freezer and incubated at −20° C. for 10 minutes. After the incubation the 96-well plate was transferred immediately to a plate-reader. $\lambda_{ex}$=290 nm, $\lambda_{em}$=370 nm, cutoff at $\lambda$=325 nm.

The elution samples were also analyzed for activity of the rabbit antibody molecule using an Enzyme-Linked Immunosorbent Assay (ELISA). Briefly, the wells of 96-well plates were first coated with a goat IgG (Sigma, St. Louis, Mo.; catalog #15256) coating solution, incubated for 90 minutes at room temperature, and then washed 3× with 300 µL PBS/Tween 20 (Sigma). The wells were blocked with 200 µL StabilCoat (SurModics, Eden Prairie, Minn.) for 1 hour at room temperature and then washed 3× with 300 µl PBS/Tween 20. A 100 µl aliquot of elution solution (from the elution of Fab from the polymeric matrices) was added to the appropriate wells and incubated for 1 hour at room temperature, and then washed 3× with PBS/Tween 20. A 100 µL sample of 0.1 µg/mL donkey anti-rabbit IgG HRP (Rockland Immunochemicals, Gilbertsville, Pa.; catalog #611-703-127) was added to each well and incubated for 1 hour at room temperature. The wells were washed 4× with 300 µL PBS/Tween 20. A 100 µL of TMB Microwell Peroxidase Substrate System (KPL, catalog #50-76-00; Gaithersburg, Md.) was added to each well. For kinetic assays, the TMB substrate produces a blue color upon reaction with peroxidase. After 15 minutes, the 96-well plate was analyzed for HRP conjugate on a spectrophotometer (Molecular Devices) at 650 nm absorbance. For endpoint analysis, addition of an acidic stop solution will halt color development and turn the TMB substrate yellow. Alternatively, after 15 minutes, 100 µL of a 1N HCl solution was added to the well to stop the reaction. Absorption was then measured at 450 nm. Any variations or modifications to the ELISA Assay are noted in the Examples.

The following polymers were used in the examples. Poly (butyl methacrylate)(pBMA) and poly(ethylene-co-vinyl acetate)(pEVA) are described in Example 1 of U.S. Pat. No. 6,214,901. pBMA/pEVA polymer matrices are available from SurModics (Eden Prairie, Minn.) under the product name BRAVO™. The polymer PEG$_{1000}$-45PBT-55 is a copolymer of poly(butyleneterephthalate-co-ethylene glycol) copolymer with 45 wt. % polyethylene glycol having an average molecular weight of 1000 kD and 55 wt. % butyleneterephthalate. PEG$_{1000}$-45PBT-55 is commercially available from OctoPlus (Leiden, Netherlands) under the product name PolyActive™ The macromer "MD-acrylate" is an acrylated maltodextrin polymer prepared as described in U.S. Patent Publication No. 2007/0065481. Polyvinyl pyrrolidone (PVP) Kollidion 90F was obtained from BASF Mt. Olive, N.J. (cat #85-2549). Poly(ethylene glycol) (PEG) was obtained from Union Carbide, Danbury, Conn. (#37255-26-6).

The photo-reagent 4,5-bis(4-benzoylphenylmethyleneoxy)benzene-1,3-disulfonic acid disodium salt (DBDS) was prepared as described in Example 1 of U.S. Pat. No. 6,669,994.

Colloidal Gold 5 nm, 0.01% w/v, 5 µg gold, 0.00013% w/w protein, was purchased from VWR, West Chester, Pa. (cat # IC15401005).

Spray coating was performed using an Ultrasonic Spray Coater as described U.S. Published Application 2004/0062875, or an IVEK Coater having asyringe pump connected to an IVEK gas atomization spray system (DIgispense 2000 Model #4065, IVEK, North Springfield, Vt.) as described in U.S. Published Application 2005/0244453.

Example 1

Formation of Microparticles Containing IgG and a Degradable Polymer

A solution of IgG (10% Rabbit anti Goat, 90% non-specific Rabbit) (Sigma, St. Louis, Mo.) at a concentration of 3.54 mg/mL in 5 mM phosphate buffer was prepared. MD-acrylate was added to phosphate buffered solution at a concentration of 10 mg/mL. The MD-acrylate solution was added to the IgG in different ratios. Total solids were kept at 1.7 mg. A 20 mg/mL of PVP was added to the combined MD-acrylate and IgG solution, causing formation of MD-acrylate/IgG microparticles. The solution with PVP was then lyophilized (frozen on dry ice and kept under high vacuum over night, sample at room temperature).

The photoinitiator tetrakis(4-benzoylbenzyl ether) of pentaerythritol ("tetra-BBE-PET"), prepared as described in U.S. Pat. No. 5,414,075 (Example 1), at a concentration of 10 mg/mL in chloroform, was added to the lyophilized MD-acrylate/IgG microparticles in an amount of 0.2 equivalent to the MD-acrylate. The solution was vortexed well and placed in a Dymax Lightweld PC-2 illumination system (Dymax Corp. Torrington, Conn.; 330-340 nm, light intensity 6.5 mW/cm$^2$) to promote crosslinking of the MD-acrylate. The solution was located at a distance of 30 cm from light source, illuminated for 240 seconds, and then removed. The mixture was spun at 5000 rpm for 5 minutes and the chloroform discarded. The residue was washed 2 times in chloroform.

The solids were taken up in 1 mL of deionized (DI) water and samples were transferred onto a plate for analysis by light microscopy. Microparticles were seen at 500× and 1000× magnification. The sizes of the microparticles were approximately 1 to 2 microns.

Example 2

Formation of Microparticles Containing IgG and a Degradable Polymer

A solution of IgG (10% Rabbit anti Goat, 90% non-specific Rabbit (Sigma, St. Louis, Mo.)) at a concentration of 3.54 mg/ml in 5 mM phosphate buffer was prepared. Dextran glycidyl methacrylate (as described in U.S. Pat. No. 6,303,148; and commercially available under the tradename "Octodex™") was added to water to a concentration of 10 mg/mL. The dextran glycidyl methacrylate solution was then added to the IgG in different ratios. Total solids was kept at 1.7 mg. To the aqueous solution 20 mg PVP was added and lyophilized. A solution of tetra-BBE-PET in at 10 mg/mL in chloroform was added to the lyophilized IgG/dextran glycidyl methacrylate microparticles in 0.2 equivalent to the dextran glycidyl methacrylate. The solution was vortexed well and placed in a Dymax Lightweld PC-2 illumination system (Dymax Corp.; 330-340 nm, light intensity 6.5 mW/cm$^2$). The solution was located at a distance of 30 cm from light source, illuminated for 240 seconds, and then removed. The mixture was spun at 5000 rpm for 5 minutes and the chloroform was discarded. The residue was washed 2 times with chloroform.

Example 3

Formation of Microparticles Containing IgG and an Amphiphilic Polymer

An 11 mL aliquot of PBS containing 11 mg specific Rabbit anti-Goat IgG and 100 mg non-specific Rabbit IgG (both from Lampire Biological Laboratories, Inc., Pipersville, Pa.) was divided into 4 portions of 2.75 mL and run through a desalting column (Econopac 10DG, Bio-Rad) with 5 mM phosphate buffer. To the eluent 2 grams of polyvinylpyrrolidone (PVP) was added in 40 mL deionized water (DI). The solution was treated for 2 hours at −20° C., 2 hours at −5° C., 2 hours at 20° C., 24 hours at 0° C., then lyophilized. PVP was then extracted by suspending solids in chloroform, spinning the protein down, and aspirating the solvent.

Example 4

Characterization of Microparticles Containing IgG and PVP Using Size Exclusion Chromatography (SEC)

Two samples of microparticles made according to the method described in Example 3 were analyzed to determine the residual concentration of PVP. The samples were transferred to an 8 mL vial and weighed (26 mg and 27 mg). A 1.75 ml aliquot of water was added, and the solution was gently shaken to dissolve/suspend the microparticles. Both solutions for the analyzed samples were initially cloudy, but with the dropwise addition of 0.5% acetic acid, one solution cleared entirely, while the second cleared somewhat. Dropwise addition of acetonitrile (ACN) cleared this solution somewhat more, but not entirely, and further addition of ACN resulted in the intended effect of flocculation of the protein in both samples; an apparently large amount of protein was flocculated in both sample solutions.

The extracts were centrifuged, and the supernatant was evaporated under nitrogen at 75° C. to a final volume of either 100 μL or 150 μL. The solutions were filtered through polypropylene filters. Upon evaporation to the final volume, both extracts showed an abundance of white precipitate. An injection solvent (63% MeOH with 50 mM ammonium acetate buffer (pH 6.8)) was added to the samples and then size exclusion chromatography (SEC) was performed on the samples. Both samples showed a broad and offscale peak that eluted in the same retention time range as the PVP standard. A dilution of one of the sample extracts confirmed that the material corresponded approximately to the retention time of the polyvinylpyrrolidone (PVP) standard. The concentration of PVP was estimated to be between 0.5 wt. % and 2.0 wt. % in both of these samples, using an extrapolation of the calibration curve. Thus, microparticles made according to the method described in Example 3 have between about 0.5 wt. % and 2.0 wt. % PVP.

Example 5

Formation of Coating Including Microparticles in Degradable Matrix

IgG (Rabbit anti-Goat) 2.4 mg was dialyzed and co-lyophilized with PVP (50 mg) as described in Example 3, for the preparation of IgG microparticles. The PVP was extracted with chloroform by spinning (5 krpm, 5 minutes) and resuspension several times (≧3). IgG particles in an amount of 1 mg were mixed with 100 mg of polymer "4-L-L-Phe-4-PEA" (prepared as described in U.S. Pat. No. 6,703,040 (Table 2, legend, last line) in 5 mL chloroform. The suspension was homogenized using an ultrasonic probe (15 sec, pulses of 0.5 sec). The suspension was sprayed onto parylene coated metal MP-35N alloy coils (Lake Region Manufacturing, Inc., Chaska, Minn.) using gas-atomization type spray equipment at three different total IgG amounts (8.0 ug IgG, 9.9 ug IgG, and 30.0 ug IgG—but all at a loading of 0.8 wt. % IgG). Specifically a 1 gram charge of Parylene-C dimer was deposited over each coil using a standard vapor deposition process.

The release rate of the IgG from the coated coils was then evaluated as follows. Coated coils were placed in microcentrifuge tubes in 500 μL of a solution of 1×PBS. At predetermined intervals the eluent was removed from the microcentrifuge tube, and 0.5 mL of fresh eluent solution (1×PBS) was added to the microcentrifuge tube having the coil. The eluent samples in 96 well plates were analyzed for activity of the Rabbit antibody molecule using an Enzyme-Linked Immunosorbent Assay (ELISA) as described herein.

Detectable antibody was found in the eluate samples at each timepoint. The percentage elution of active IgG is shown below in Table 1 as a percentage of total active IgG. The results are also shown in FIG. 1. The release at 0.8% w/w loading was found to be about 0.1 μg per day for all coatings. The thinner the coating (less amount of protein), the faster the relative release (percent release).

TABLE 1

| Time (Days) | Sample 1 4-L-L-Phe-4-PEA (8.0 ug IgG, 0.8%) | Sample 2 4-L-L-Phe-4-PEA (9.9 ug IgG, 0.8%) | Sample 3 4-L-L-Phe-4-PEA (30 ug IgG, 0.8%) |
|---|---|---|---|
| 0.1 | 1.26 | 0.91 | 0.34 |
| 1.25 | 2.52 | 1.81 | 1.27 |
| 2.7 | 4.56 | 2.24 | 1.79 |
| 4 | 5.86 | 2.54 | 3.79 |
| 5.3 | 8.10 | 3.72 | 4.95 |
| 7 | 11.51 | 4.97 | 5.89 |
| 9 | 24.48 | 27.63 | 7.07 |
| 11 | 27.96 | 29.25 | 8.02 |
| 14 | 31.67 | 31.06 | 8.71 |
| 17 | 32.44 | 31.94 | 9.19 |
| 21 | 32.93 | 33.94 | 9.79 |
| 25 | 33.18 | 34.23 | 10.24 |
| 29 | 37.51 | 38.68 | 11.41 |
| 32 | 40.33 | 40.95 | 12.56 |
| 35 | 44.79 | 43.38 | 14.20 |
| 39 | 47.48 | 45.14 | 15.26 |
| 42 | 50.26 | 47.21 | 16.16 |
| 45 | 51.08 | 48.30 | 16.44 |

Example 6

Formation of Coating Including Microparticles in a Non-Degradable Polymeric Matrix A 2 g aliquot of PVP was dissolved with 100 mg non-specific Rabbit IgG and 11 mg Rabbit IgG-antiGoat in 11 mL PBS. After lyophilization the PVP was extracted with chloroform by repeated centrifugation and resuspension in fresh chloroform (at least 3 times). A suspension was obtained of IgG and residual PVP (1-2 wt. %); the material was amorphous (having a clumpy appearance). A weighed amount of dry IgG powder was resuspended in chloroform at 20 mg/ml. $PEG_{1000}$-45PBT-55 was added to the suspension obtaining a final concentration of 10 mg/mL. The suspension was filtered through a 20 micron filter and then loaded in a 5 mL Hamilton glass syringe, equipped with a micro stirrer and mounted in a syringe pump. In a second 5 mL Hamilton glass syringe a coating solution was loaded consisting of pEVA and pBMA at a of 4 mg/mL and 16 mg/mL, respectively, (20 mg/ml total polymer) in a chloroform. The two solutions were then simultaneously sprayed onto stents using an ultrasonic spray system as described in U.S. Published Application. No. 2007/0128343, entitled "Apparatus and Methods for Applying Coatings," filed Nov. 14, 2006. The coating conditions were generally kept constant (1.5 W, 3.5 psi, 100 coating cycles). The flow ratio for the solutions being delivered to the coating heads was 0.06 mL/min combined, and divided between the protein suspension and the polymer solution according to Table 2:

TABLE 2

| Test Set (protein loading) | Protein Suspension Spray Rate | Polymer Solution Spray Rate |
| --- | --- | --- |
| 1 (150 ug total IgG, 40% w/w) | 0.03 ml/min | 0.03 ml/min |
| 2 (184 ug total IgG, 30% w/w) | 0.02 ml/min | 0.04 ml/min |

The elution rate of the IgG from the stents was then tested. The stents were put into 1 ml of PBS and portions of the solution were periodically tested for both total IgG content and active IgG content. Active protein release was assessed with an ELISA assay according to the procedures described above. Active protein release as a percentage of total active protein (e.g. specific IgG) is shown in Table 3 and in FIG. 2.

TABLE 3

| Time (hrs) | Test Set 1 | Test Set 2 |
| --- | --- | --- |
| 1 | 1.23 | 3.23 |
| 2 | 5.76 | 7.32 |
| 3 | 5.85 | 7.96 |
| 6 | 6.52 | 8.97 |
| 8 | 6.88 | 10.74 |
| 13 | 8.43 | 13.75 |
| 17 | 8.95 | 14.55 |
| 24 | 9.25 | 15.40 |
| 31 | 9.93 | 17.34 |
| 36 | 10.02 | 18.07 |
| 43 | 10.03 | 18.93 |
| 50 | 10.63 | 19.68 |
| 55 | 10.63 | 19.83 |

Figure 3:
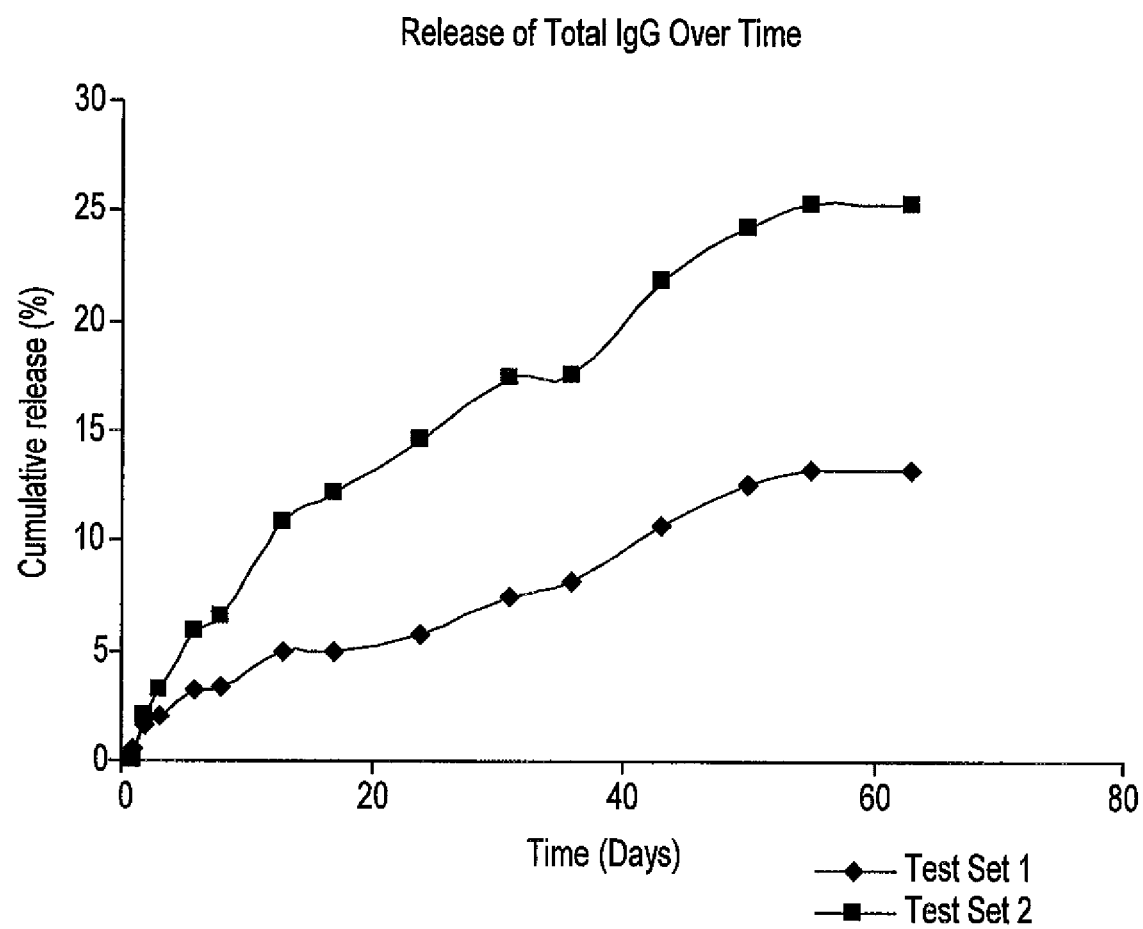

Total protein was measured with BCA total protein kit (Sigma, St. Louis, Mo.) or using the Bradford reagent (Sigma, St. Louis, Mo.). Elution of total protein is shown in Table 4 and in FIG. 3.

TABLE 4

| Time (hrs) | Test Set 1 | Test Set 2 |
| --- | --- | --- |
| 1 | 0.58 | 0.057 |
| 2 | 1.57 | 1.95 |
| 3 | 1.95 | 3.23 |
| 6 | 3.21 | 5.87 |
| 8 | 3.31 | 6.52 |
| 13 | 5.01 | 10.88 |
| 17 | 5.01 | 12.22 |
| 24 | 5.77 | 14.58 |
| 31 | 7.49 | 17.41 |
| 36 | 8.19 | 17.58 |
| 43 | 10.75 | 21.78 |
| 50 | 12.66 | 24.29 |
| 55 | 13.20 | 25.29 |
| 63 | 13.20 | 25.37 |

Example 7

Coil Coating of IgG Microparticles in pBMA/pEVA/PEG$_{1000}$-45PBT-55 Matrix and IgG Elution IgG protein particles were made by phase separation in PVP. A 150 mg sample of IgG in 10 mg/mL in PBS was desalted using Bio-Rad Econo-Pac 10 DG (Bio-Rad, Hercules, Calif.). The IgG was eluted from the column in 5 mM PBS. To the solution 3 grams of PVP was added, frozen and lyophilized. The PVP was extracted using chloroform. Before using the ultrasonic spray coater, the suspension of IgG particles in chloroform was passed through a 20-micron polypropylene filter using a Buechler funnel. The IgG particles were then dispersed in a pBMA/pEVA/PEG$_{1000}$-45PBT-55 coating solution. A 40% w/w protein loading of IgG/PEG$_{1000}$-45PBT-55 in a 2:1 ratio was made. Compositions were prepared to provide pBMA/pEVA ratios of 1:1 or 1:4. Spray coatings of the solutions were done on the ultrasonic spray coater as well as by using an IVEK coater. In Table 5, a total 6 coils were coated using the IVEK coater and 3 coils (coils 7-9) were coated with the ultrasonic spray coater with the following coating weights:

TABLE 5

| Coil | pBMA/pEVA ratio | IgG/PEG$_{1000}$-45PBT-55 ratio (w/w) | Coating weight (mg) | IgG loading (mg) |
| --- | --- | --- | --- | --- |
| 1 | 1:1 | 2:1 | 4.10 | 1.64 |
| 2 | 1:1 | 2:1 | 1.41 | 0.56 |
| 3 | 1:1 | 2:1 | 0.95 | 0.38 |
| 4 | 1:4 | 2:1 | 1.02 | 0.41 |
| 5 | 1:4 | 2:1 | 1.04 | 0.42 |
| 6 | 1:4 | 2:1 | 1.20 | 0.48 |
| 7 | 1:4 | 2:1 | 0.47 | 0.188 |
| 8 | 1:4 | 2:1 | 0.522 | 0.2088 |
| 9 | 1:4 | 2:1 | 0.527 | 0.2108 |

Figure 5:
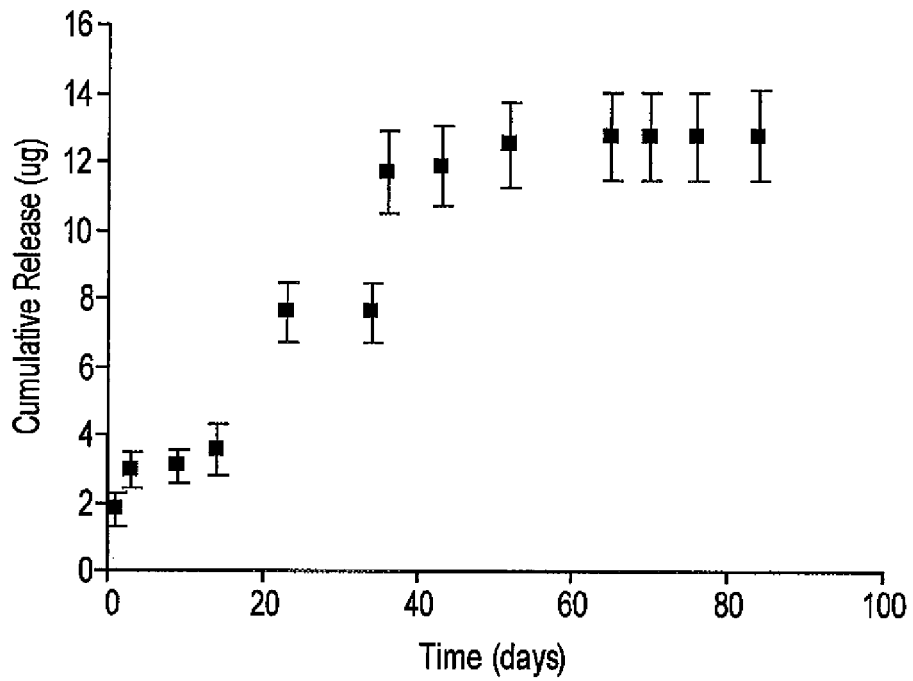

FIGS. 4 and 5 shows the cumulative, release of IgG protein from coatings formed using either an IVEK coater or ultrasonic spray coater spraying system. The elution of IgG protein was conducted in PBS and measured using ELISA.

The release of IgG from coatings formed from the ultrasonic spray coater stopped after approximately 90 days. The release of IgG from coatings formed from the IVEK coater showed a prolonged release of IgG (>150 days). The coating generated with IVEK coater appeared coarser under visual inspection relative to the ultrasonic spraying system. There appeared to be phase-separation of the pBMA and pEVA polymeric components.

Example 8

IgG Released IgG/MD-Acrylate Particles

An aqueous IgG solution was prepared consisting of 10% specific rabbit-α-goat and 90% non-specific protein (Lampire). MD-acrylate was dissolved in the IgG solution at a 1:2 IgG:MD-Acrylate w/w ratio. Particles were obtained by slowly mixing in a 30% w/v PEG 20 kDa solution with 0.5 mg/ml DBDS while vortexing the IgG:MD-Acrylate solution. By adding DBDS to the PEG-phase the formed particles could be crosslinked. The crosslinked particles were formed by a 5 minute-UV irradiation. UV irradiation was done in the cold room using Dymax lamp at 4° C. while stirring the PEG-particle suspension on ice. Resultant particles were isolated by centrifugation at 5 k rpm for 10 minutes. Remaining PEG was further removed by adding 5 mL isopropyl alcohol (IPA) to the residue. The suspension was vortexed and spun at same settings. The washing with IPA was repeated. Subsequent washing was done with 5 ml chloroform.

Figure 6:
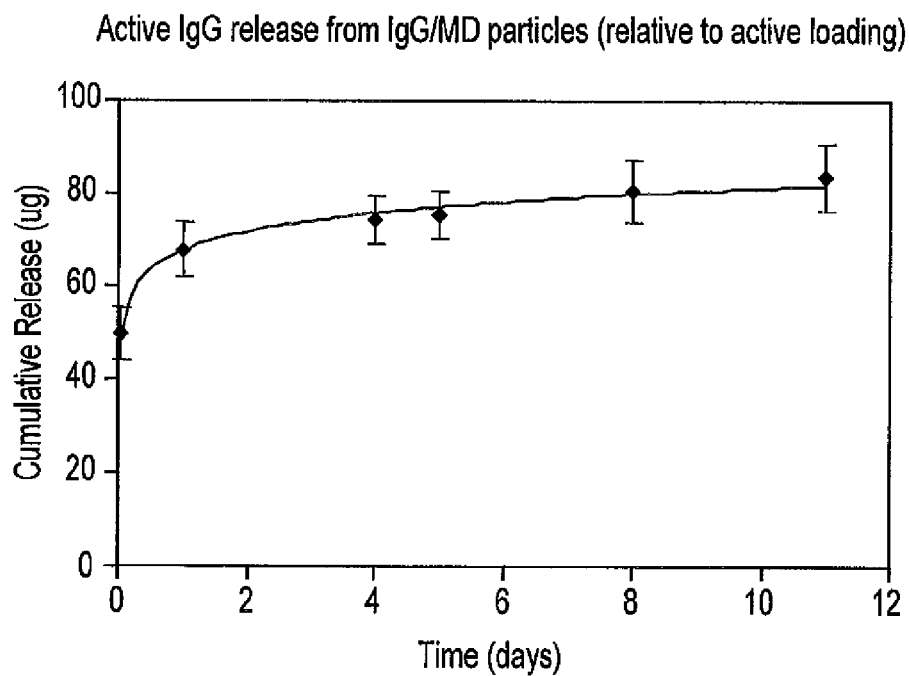

A weighed amount of IgG/MD-Acrylate particles (10 mg) were incubated in 1 mL of PBS to characterize the release kinetics. In FIG. 6, a burst is seen of around 50% in the first hour. This burst is caused by particles that consist of mostly of either IgG alone or by particles with uncompleted crosslinking. Using the ELISA assay, a total release of about 85% (active IgG w/w total active IgG) was measured, over 11 days and the particles were still releasing functional IgG protein.

Example 9

Coil Coating of IgG/MD-Acrylate Microparticles in pBMA/pEVA/PEG$_{1000}$-45PBT-55 Matrix and IgG Elution IgG/MD-Acrylate particles described above were loaded into a pBMA/pEVA/PEG$_{1000}$-45PBT-55 coating solution at 30% w/w IgG/MD-acrylate. A polymeric coating composition was prepared as indicated in Table 5. In a 15 ml chloroform suspension of particles comprised of a mixture of IgG and crosslinked compound III in 1:2 ratio at 0.83 mg/ml, 6.3 mg of PEG$_{1000}$-45PBT-55, 12.5 mg pEVA, and 12.5 mg pBMA were dissolved while shaking the mixture for 30 minutes on an orbital shaker at 37° C. Four coils were coated. The total loading of IgG on the substrate was approximately 50 µg. (150 µg IgG/MD particle in 500 µg coating). Results indicated that 10% of the IgG was active (approximately 5 µg). An additional topcoat with pEVA/pBMA 1:1 ratio was applied to coil numbers 9 and 10. See Table 8 for coating weights. The coating solution, pBMA/pEVA/PEG$_{1000}$-45PBT-55, and particle matrix IgG/MD-acrylate(MD) is described in Table 6.

TABLE 6

| Coil # | IgG | MD | PEG$_{1000}$-45PBT-55 | PBMA | pEVA | pEVA/pBMA top coat (tc) | Coating wt. (ug) | Total IgG (ug) | Active IgG (ug) |
|---|---|---|---|---|---|---|---|---|---|
| 1 | 9.5 | 19 | 14.6 | 28.6 | 28.6 | | 0.485 | 46.075 | 4.6075 |
| 2 | 9.5 | 19 | 14.6 | 28.6 | 28.6 | | 0.5 | 47.5 | 4.75 |
| 3 | 9.5 | 19 | 14.6 | 28.6 | 28.6 | 0.228 | 0.458 | 43.51 | 4.351 |
| 4 | 9.5 | 19 | 14.6 | 28.6 | 28.6 | 0.259 | 0.474 | 45.03 | 4.503 |

The particle matrix suspension was very fine and extremely stable. The obtained coatings were smooth under visual inspection. Total loading of IgG is approximately 50 µg (150 µg IgG/MD particle in 500 µg coating). The final coating weight was approximately 500 µg.

Figure 7:
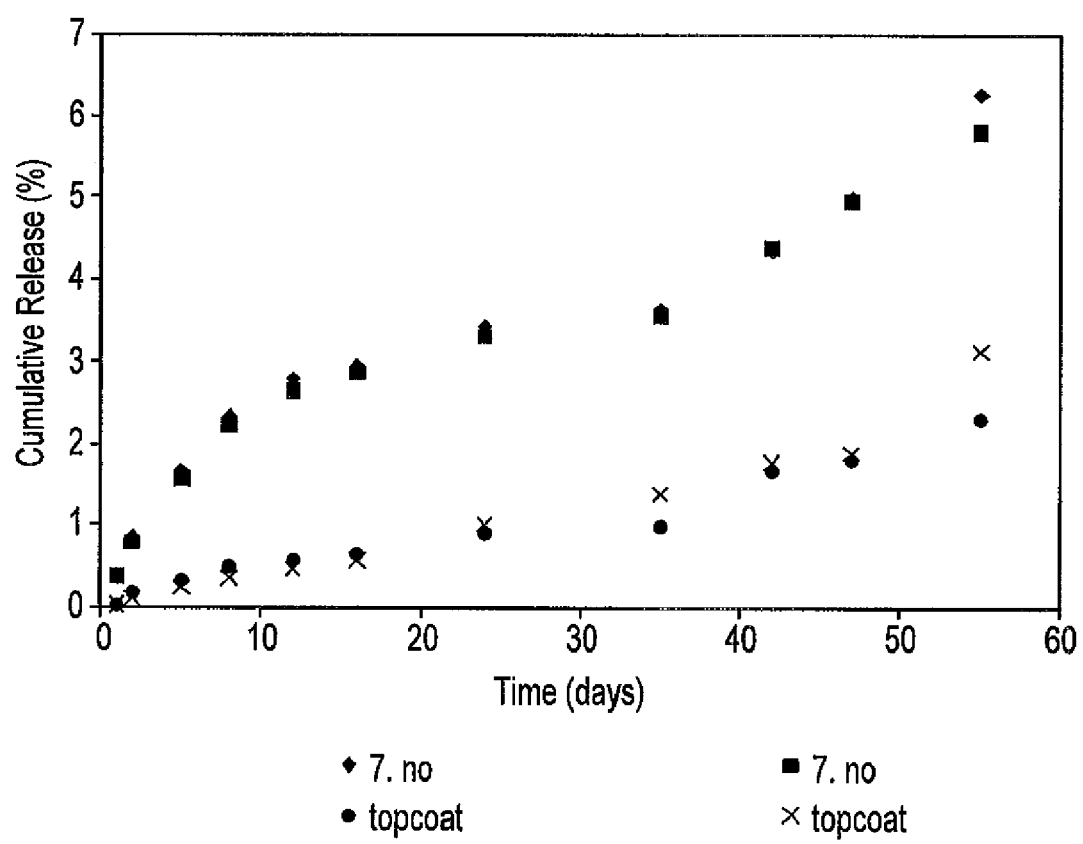

FIG. 7 shows the results for the controlled release of IgG from the IgG/MD-acrylate particles in the pBMA/pEVA/PEG$_{1000}$-45PBT-55 coating solution from four coils. The addition of a pBMA/pEVA topcoat, provides additional control of the release of IgG.

Active IgG was measured by ELISA. Table 7 shows the controlled release of active IgG with and without topcoats up to 55 days.

TABLE 7

| time (days) | Coil 1 (µg) | Coil 2 (µg) | Coil 3 PEVA/PBMA topct (µg) | Coil 4 PEVA/PBMA topct (µg) |
|---|---|---|---|---|
| 1 | 0.394759 | 0.377274 | 0.058946 | 0.029214 |
| 2 | 0.856479 | 0.780211 | 0.185544 | 0.09542 |
| 5 | 1.671243 | 1.545421 | 0.347225 | 0.244592 |
| 8 | 2.317287 | 2.196568 | 0.515295 | 0.359333 |
| 12 | 2.771118 | 2.645374 | 0.607177 | 0.471752 |
| 16 | 2.952089 | 2.870442 | 0.672058 | 0.566489 |
| 24 | 3.426574 | 3.289229 | 0.905502 | 1.018827 |
| 35 | 3.634572 | 3.555892 | 1.013914 | 1.3934 |
| 42 | 4.358267 | 4.386102 | 1.656778 | 1.770998 |
| 47 | 4.98557 | 4.955655 | 1.820711 | 1.879065 |
| 55 | 6.264219 | 5.799029 | 2.307536 | 3.144327 |

Example 10

Coil Coating of IgG/MD-Acrylate Particles Microparticles in pBMA/pEVA/PEG$_{1000}$-PBT Matrix and IgG Elution The Fab protein was prepared using a series of column elutions and centrifuge steps. Four Bio-Rad columns were prepared as described in Example 7. Storage buffer was disposed. Columns were eluted with 20 ml 5 mM PBS. 2.5 ml of Fab (specific rabbit-α-goat and 90% non-specific protein (Southern Biotech, Birmingham, Ala.), A280(50 µl)=0.898, ε=1.35=>13.3 mg/ml. The PBS Fab solutions were put into each column and were permitted to be absorbed completely. The columns were then filled completely with 5 mM PhosphateBuffer w/o NaCl (pH=7.31). Elution samples were collected of approximately 1 ml each and analyzed at A280. The first 4 fractions of all 4 columns were combined: ~19 ml A280=0.491, conc=7.27 mg/ml.

Two centrifuge filters (10 kDa cutoff, Pall, East Hills, N.Y.) were filled with 3.5 ml of the Fab protein solution and spun at 5500 g for 50 minutes at 6° C. To the remaining supernatant, a 3 ml aliquot of the remaining solution was added to a centrifuge filter and spun under the same conditions for 50 minutes. The supernatants were combined and added to the remaining 6 ml solution. The combined fractions had a protein concentration of 21.5 mg/ml based on A280(50 µl)=1.452, yielding a total of 130 mg Fab.

Particles were formed by placing the protein solution in a 50 ml centrifuge tube with hole in screw-cap at 37° C. for 10 minutes. A pre-heated to 37° C. 30% w/v PEG 20 kDa solution, 8.67 ml, was added to the protein solution through the hole in the cap while vortexing. A white suspension was formed and pored into a plastic Petri-dish. The dish was covered and treated to consecutively lower temperatures of 4° C. for 1 hour, −20° C. for 1 hour and dry ice for 30 minutes. The initially glossy appearance of the PEG/protein suspension became matted and solid. The frozen suspension was put for lyophilization in a vacuum oven at room temp over night (vacuum 30 mm Hg)

Once no soft or moist spots were noticed by visual inspection, the dry cake was transferred to a 50 ml centrifuge tube and placed at −20° C. for 2.5 days. A 20 ml aliquot of HPLC grade chloroform was added. The PEG dissolved rendering a cloudy fine protein suspension. The chloroform was dispensed into two 15 ml tubes and centrifuged at 5000 rpm at 4° C. for 10 minutes. Using glass pipettes, the chloroform was aspirated and stored. Fresh chloroform (10 ml per tube) was added. This washing procedure was done 3 times in total. The protein particles were then combined in 10 ml chloroform and spun at 5000 rpm for 10 minutes at 4° C. The chloroform was aspirated off and protein particles were resuspended in 10 ml chloroform. The remaining Fab protein particles from aspirated chloroform fractions were retrieved separately, washed 2 times and added to the main batch.

The suspension was homogenized with a hand-held homogenizer at 21 krpm and subsequently filtered through a 20 μm polypropylene filter (Buchner filter). All Fab particles passed the filter. The filtered batch was collected in a 20 ml boronated glass vial.

The concentration of the Fab protein particles was measured in duplicate. A 50 μl of the suspension was dispensed on a glass cover slip and weighed. The cover slip was placed in a plastic Petri-dish and washed with 1 ml of 5 mM PBS. The PBS was analyzed for protein concentration at A280. A 200 μl aliquot was sampled and stored at 4° C. Table 8 summarizes the characteristics of the Fab protein preparation prior to formulating a coating solution.

TABLE 8

| Sample | Solids | Conc | A280 | Conc |
|---|---|---|---|---|
| 1 | 0.311 mg | 6.22 mg/ml | 0.349 | 5.17 mg/ml |
| 2 | 0.302 mg | 6.04 mg/ml | 0.340 | 5.03 mg/ml |

A coating formulation was made by transferring 14 ml of the Fab suspension in chloroform to a clean boronated glass vial. The total weight of the Fab particles was 72.38 mg. A 36.19 mg amount of PolyActive was added to the Fab suspension and shaken until the PolyActive was dissolved. The Fab/PolyActive mixture was stored at −20° C. overnight, approximately 8 hours.

A coating of 66.6 mg amount of pBMA and a 66.6 mg amount of pEVA was added to the Fab microparticle $PEG_{1000}$-45PBT-55 mixture. The final weight percents for the components of the Fab microparticle/pBMA/pEVA/$PEG_{1000}$-45PBT-55 coating solution was 29.93%, 14.97%, 27.55%, 27.55%, respectively for each of the components of the coating solution. The mixture was shaken on an orbital shaker, 200 rpm, at 32° C. for 60 minutes prior to coating the coils by spray deposition. A total of eight coils were coated with the ultrasonic spray coater and 300 μg of Fab protein was loaded on each coil. After drying over night in a nitrogen box a Parylene-C topcoat was applied (1 gr monomer was used). Specifically a 1 gram charge of Parylene-C dimer was deposited over each coil using a standard vapor deposition process.

Total protein and active protein were measured by ELISA and Tryptophan assay techniques for the eight coils. FIG. 8 summarizes the active protein and total protein recovered to approximately 120 days for each of four coils describing the two curves. Over 85% active protein was detected out to approximately 120 days.

Example 11

Fab-Microparticle Coating Formulations with Different pBMA/pEVA/$PEG_{1000}$PBT Ratios The Fab protein was prepared using a series of column elutions and centrifuge steps. Four Bio-Rad columns were prepared by disposing the storage buffer and elude with 20 ml 5 mM PBS, pH 7.3. 2.5 ml of Fab 14.1 mg/ml (RαG Southern Biotech), $A_{280}$(50 μl)=0.953, was put on each column and permitted to be completely absorbed. The columns were then filled completely with 5 mM PBS. Elution samples were collected of approximately 1 ml each and analyzed at A280. The first 4 fractions of two pairs of columns were combined. Four centrifuge filters (10 kDa cutoff, Pall, East Hills, N.Y.) were filled with 3 ml protein solution and spun at 5500 g for 50 minutes at 6° C. To the remaining supernatant the rest of the solution was added and spun under same conditions for 10 minutes. The supernatants were combined yielding 5.5 ml of 22.52 mg/ml Fab.

Particles were formed be placing the protein solution in a 50 ml centrifuge tube with hole in screw-cap and heating the tube to 37° C. for 10 minutes. A 6.67 ml of a 30% w/v PEG 20 kDa solution, pre-heated to 37° C., was added to the protein solution through the hole in the cap while vortexing. A white suspension was formed and pored into a plastic Petri-dish. The dish was covered and treated to consecutively lower temperatures of 4° C. for 1 hour, −20° C. for 1.5 hour and on dry ice for 30 minutes. The initially glossy appearance of the PEG/protein suspension became matted and solid. The frozen suspension was lyophilized in a vacuum oven at room temp over night (vacuum 30 mm Hg)

Once no soft spots were noticed in the lyophilized powder by visual inspection, the dry cake was transferred to a 50 ml centrifuge tube. A 20 ml aliquot of HPLC grade chloroform was added. The PEG dissolved rendering a cloudy and fine protein suspension. The chloroform was dispensed into two 15 ml tubes and centrifuged at 5000 rpm at 4° C. for 10 minutes. Using glass pipettes the chloroform was aspirated and stored. Fresh chloroform (10 ml per tube) was added. This washing procedure was done 3 times in total. The protein particles were resuspended in 10 ml chloroform. Remaining protein from aspirated chloroform fractions were retrieved separately, washed 2 times and added to the main batch. The suspension was subsequently filtered through a 20 μm polypropylene filter (Buchner filter) and collected in a 20 ml boronated glass vial.

The concentration was measured in triplicate. A 50 μl of the suspension was dispensed on a glass cover slip and weighed. The cover slip was placed in a plastic Petri-dish and washed with 1 ml of 5 mM PBS. The PBS was analyzed for protein concentration at A280. A 200 μl was sampled and stored at 4° C.

Prior to addition of polymers the protein suspension in chloroform was homogenized using a homogenizer for 10 seconds at setting 20. The suspension was filtered through a 20-micron filter using a Buchner funnel. A coating solution was prepared according to the components listed in Table 9. The coating solution was applied to metal coils using the ultrasonic spray coater.

TABLE 9

| Coil # | Protein/$PEG_{1000}$-PBT | $PEG_{1000}$-PBT/(pBMA/pEVA) | Coating wt [ug] | % Protein | $PEG_{1000}$-PBT 1000PEG80 | $PEG_{1000}$-PBT 1000PEG55 |
|---|---|---|---|---|---|---|
| 9 | 2/1 | 1/3.7 | 1000 | 30% | 100% | |
| 10 | | | | | 80% | 20% |
| 11 | | | | | 50% | 50% |
| 12 | | | | | 20% | 80% |

Figure 9:
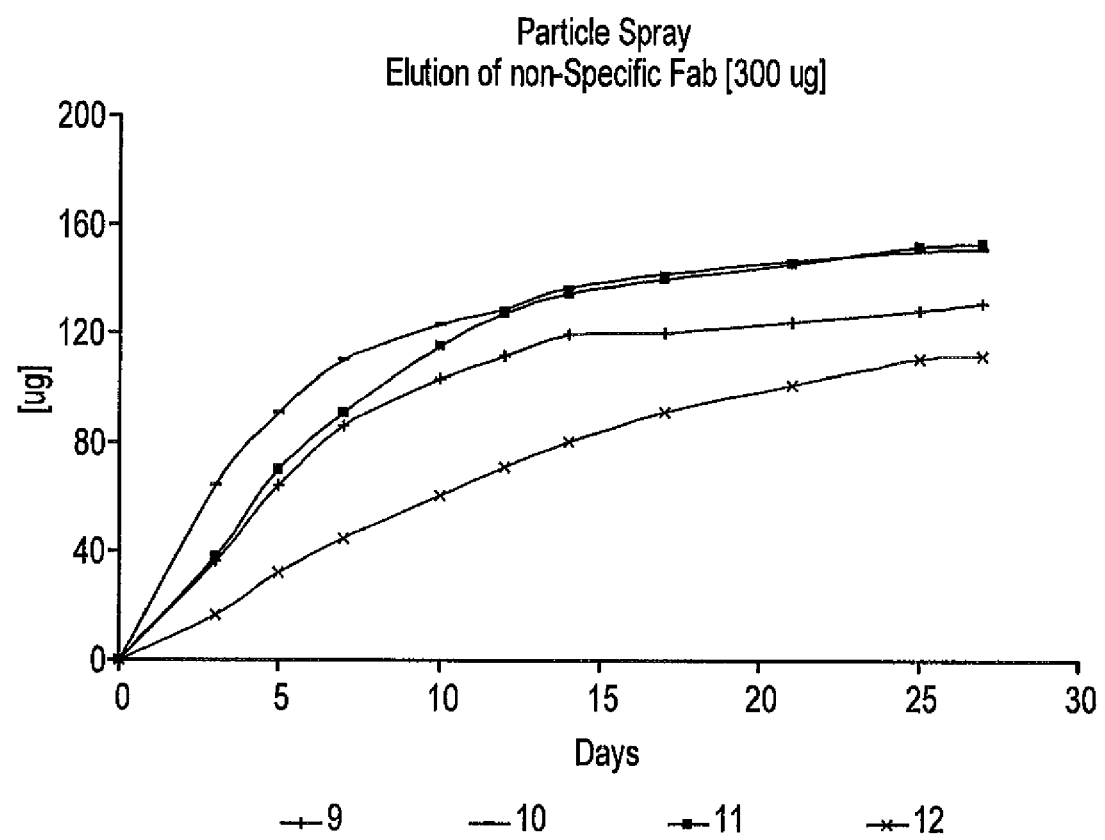

The coils were evaluated for controlled release in PBS at 37° C. Released protein was analyzed using tryptophan fluorescence. In the procedure for tryptophan fluorescence, the protein samples were denatured at room temperature by adding an equal volume of 12M guanidine solution in double distilled water. The protein samples were put at −20° C. for 10 minutes. Fluorescence was read at $\lambda_{ex}$=290 nm and $\lambda_{em}$=370 nm. FIG. 9 shows the controlled release of Fab for up to 30 days.

Example 12

Fab Microparticles Made with Colloidal Gold

The Fab protein was prepared using a series of column elutions and centrifuge steps. Four Bio-Rad columns were prepared and storage buffer was disposed. Columns were eluted with 20 ml 5 mM PBS. The 5 mM Phosphate Buffer without NaCl was prepared from a 10×PBS stock solution. A 25 ml aliquot was diluted in DI water (18.1Ω) to a total volume of 500 ml. The pH was adjusted to pH=7.31 after adding one drop of $H_3PO_4$. A 2.5 ml of Fab (RαG Southern Biotech), A280(50 µl)=0.953, ϵ=1.35=>14.1 mg/ml, was put on each column and permitted to be completely absorbed. Four ml of 5 mM PBS was put into the columns and completely eluted. Four centrifuge filters (10 kDa cutoff, Pall, East Hills, N.Y.) were filled with 4 ml of the Fab protein solution and spun at 5500 g for 50 minutes at 10° C. The supernatants were combined at Fab 20.4 mg/ml as determined by $A_{280}$. The pH of the protein solution was adjusted to 5.3. To 2 ml of Fab protein (40 mg) a 50 ul colloidal gold (5 nm, 0.01% w/v, 5 µg gold, 0.00013% w/w protein) solution was added.

To form particles, the protein/colloidal gold solution was put at 50° C. for 40 minutes in a 15 ml centrifuge tube. A 30% w/v PEG 20 kDa solution was prepared in DI water, pH adjusted to 5.0 and warmed to 50° C. A hole was drilled in the screw-cap, and 700 µl PEG, 5.25× protein weight, was dropped into the protein solution through the hole in the cap while vortexing. A slightly turbid solution was obtained and pored into a plastic Petri-dish. The dish was covered and treated at −20° C. for 1.5 hour and on dry ice for 30 minutes. The initially glossy appearance of the PEG/protein suspension became matted and solid. The frozen suspension was lyophilized (no other parameters?) in a vacuum oven at room temp over night.

Once no soft spots were noticed by visual inspection, the dry cake was transferred to a 50 ml centrifuge tube. A 20 ml aliquot of HPLC grade chloroform was added. The PEG dissolved rendering a cloudy, fine protein suspension. The chloroform was dispensed onto 4 polypropylene filters 0.2 um and centrifuged at 5500 rpm, 10° C. for 15 minutes. Using glass pipettes fresh chloroform was added. This washing procedure was done 3 times in total. The protein particles were resuspended in 10 ml chloroform. A 50 µl aliquot of the suspension was dispensed on a glass cover slip and weighed. The cover slip was placed in a plastic Petri-dish and washed with 1 ml of 5 mM PBS. The PBS was analyzed for protein concentration at A280.

Non-specific Fab particles using the nano-gold nucleation method were coated with a formulation of PolyActive/BRAVO. This coating solution uses 30% protein, 15% $PEG_{1000}$-45PBT-55, and 27.5% of both pBMA and pEVA. The coating solution was sprayed using the ultrasonic spray coater onto sample coils. Final protein loads on the coils was 300 ug. After drying over night in a nitrogen box at room temperature, a top-coat of Parylene (1 gr monomer) was applied to part of the coated coils. After spray coating, the coils were added to 500 ul of a 10 mmol PBS solution, and placed at 37° C., on an orbital shaker at 200 rpm.

Figure 10:
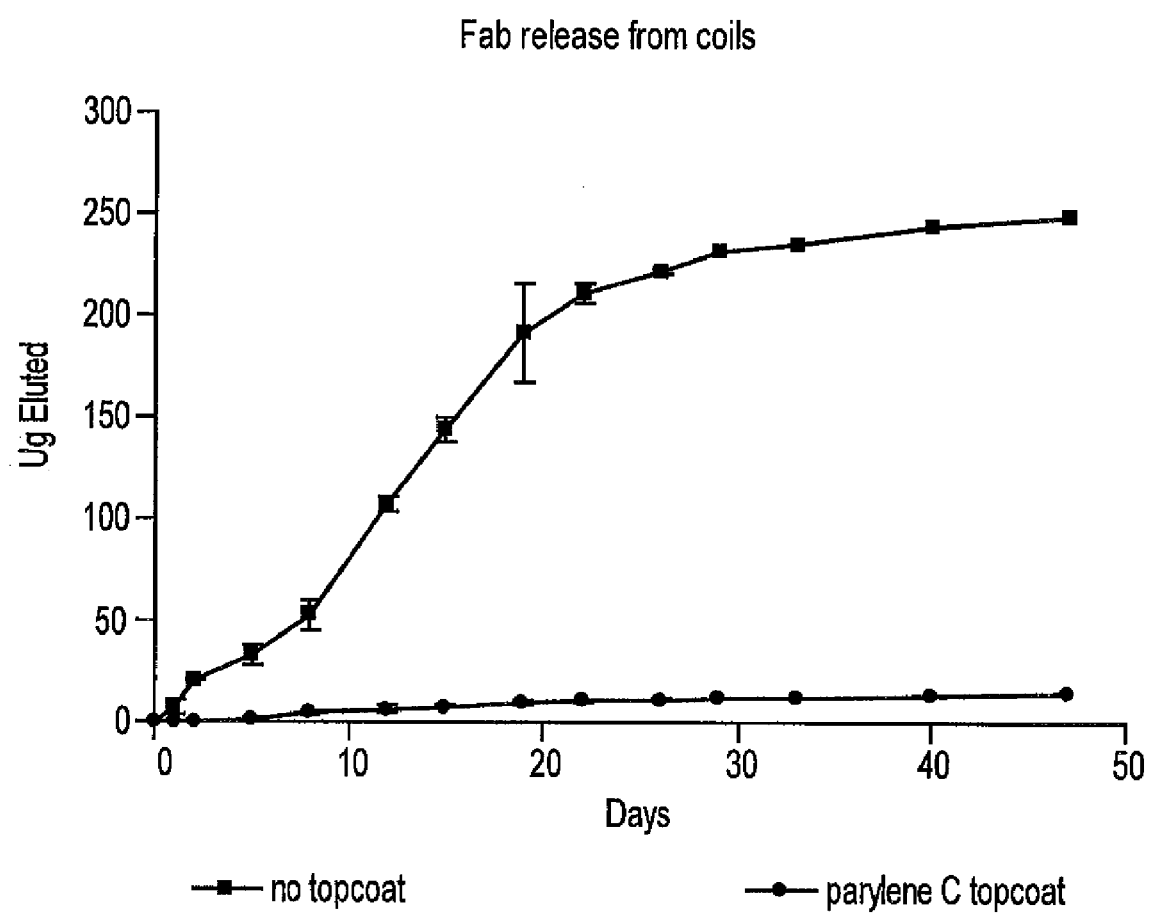

The controlled release of Fab particles from colloidal gold is seen in FIG. 10. The release profile for Fab extends out to approximately 50 days.

Example 13

Fab Particles Made with Colloidal Gold

The Fab protein was prepared using a series of column elutions and centrifuge steps. Four Bio-Rad columns were prepared and storage buffer was disposed. Columns were eluted with 20 ml 5 mM Phosphate Buffer without NaCl. 3 ml of Fab (RαG Southern Biotech), 15.2 mg/ml, was put on each column and permitted to be completely absorbed. Four ml of 5 mM PBS was put into the columns and completely eluted. Four centrifuge filters (10 kDa cutoff, Pall, East Hills, N.Y.) were filled with 4 ml of the Fab protein solution and spun at 5500 g for 50 minutes at 10° C. The supernatants were combined at Fab 20 mg/ml as determined by $A_{280}$. The pH of the protein solution was adjusted to 5.3. To 2 ml of Fab protein (40 mg) a 50 ul colloidal gold (5 nm, 0.01% w/v, 5 µg gold, 0.00013% w/w protein) solution was added.

To form particles, the protein/colloidal gold solution was put at 50° C. for 40 minutes in a 15 ml centrifuge tube. A 30% w/v PEG 20 kDa solution was prepared in DI water, pH adjusted to 5.0 and warmed to 50° C. A hole was drilled in the screw-cap, and 700 µl PEG, 5.25× protein weight, was dropped into the protein solution through the hole in the cap while vortexing. A slightly turbid solution was obtained and pored into a plastic Petri-dish. The dish was covered and treated at −20° C. for 1.5 hour and on dry ice for 30 minutes. The initially glossy appearance of the PEG/protein suspension became matted and solid. The frozen suspension was lyophilized at a benchtop lyophilizer.

The dry powder was transferred to a 15 ml centrifuge tube. 5 ml aliquot of HPLC grade chloroform was added. The PEG dissolved rendering a cloudy, fine protein suspension. The chloroform was dispensed onto 4 polypropylene filters 0.2 um and centrifuged at 5500 rpm, 10° C. for 15 minutes. Using glass pipettes fresh chloroform was added. This washing procedure was done 3 times in total. The protein particles were resuspended in 10 ml chloroform. A 50 µl aliquot of the suspension was dispensed on a glass cover slip and weighed. The cover slip was placed in a plastic Petri-dish and washed with 1 ml of 5 mM PBS. The PBS was analyzed for protein concentration at A280.

Non-specific Fab particles using the nano-gold nucleation method were coated with a formulation of pEVA/pBMA in 1:1 ratio. This coating solution uses 30% protein and 35% of both pBMA and pEVA. The coating solution was sprayed using the ultrasonic spray coater onto sample coils. Final protein loads on the coils was approximately 450 ug. After drying over night in a nitrogen box at room temperature, a top-coat of 20 mg/ml pEVA was applied to part of the coated coils. After spray coating, the coils were added to 500 ul of a 10 mmol PBS solution, and placed at 37° C., on an orbital shaker.

Figure 11:
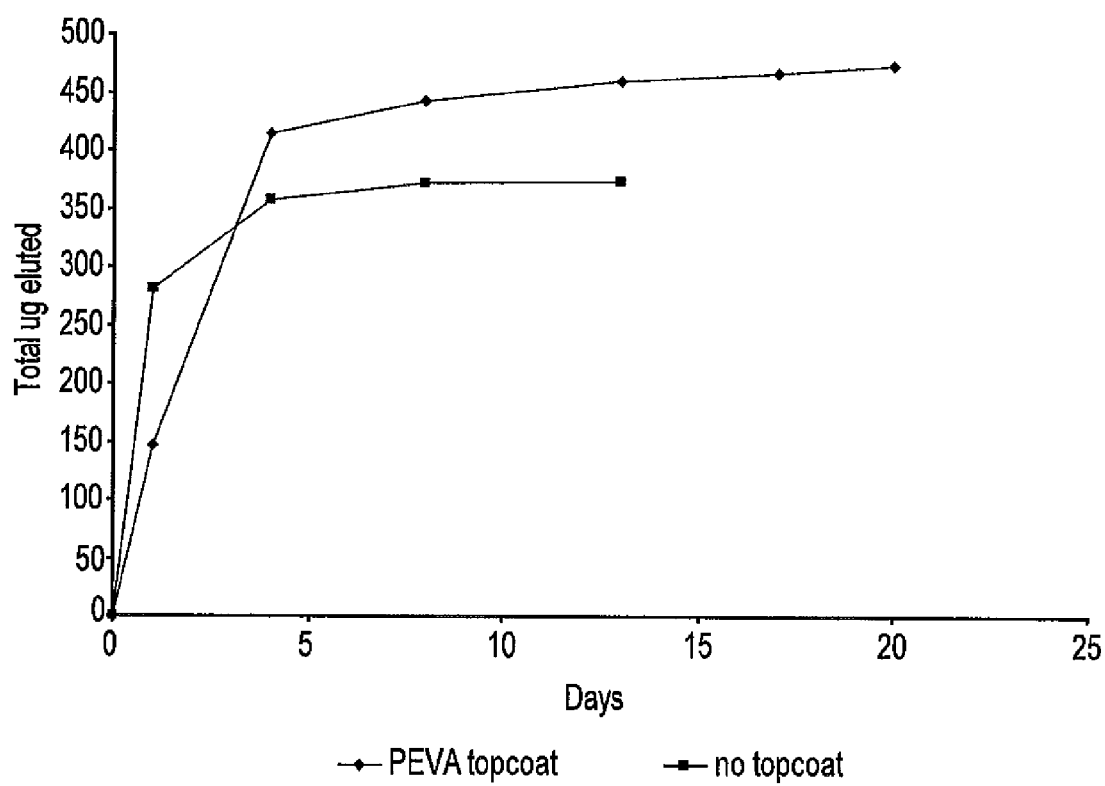

The controlled release of Fab particles from colloidal gold is seen in FIG. 11.

Example 14

Formation of Fab Microparticles with Coatings

This series of experiments studied various coating compositions on colloidal gold microparticles. A 5 mM phosphate buffer solution without NaCl was prepared from a 10×PBS stock solution. The PBS was diluted in DDW to a total volume of 500 ml. The pH was adjusted to 7.31 after adding one drop of concentrated $H_3PO_4$.

14A. Preparation of Fab Microparticles with Colloidal Gold.

Fab (rabbit anti-goat (RαG)) was desalted using a BioRad desalting column (Econo-Pac 10 DG). Storage buffer from the columns was disposed. The columns were eluted with 20 ml of 5 mM PBS. An amount of Fab (RαG), 2.5 ml, ($A_{280}$(50 µl)=0.953, $\epsilon$=1.35=>14.1 mg/ml) was put on each column and allowed to completely absorb. Fab was eluted from the columns with 4 ml of 5 mM PBS.

The Fab was then concentrated using four centrifuge filters (10 kDa cutoff, PALL LifeSciences), which were filled with 4 ml of the desalted Fab eluate and spun at 5500 g for 50 minutes at 10° C. The concentrated Fab supernatants were combined providing Fab at a concentration of 20.4 mg/ml as determined spectrophotometrically ($A_{280}$). The pH of the protein solution was adjusted to 5.3 by adding 10 µl of 2N HCl.

To 2 ml of the concentrated Fab protein (40 mg), 50 µl colloidal gold (VWR, 5 nm, 0.01% w/v, 5 µg gold, 0.00013% w/w protein) solution was added. The protein/colloidal gold solution was incubated at 50° C. for 40 minutes in a 15 ml centrifuge tube.

A PEG solution (20 kDa dissolved to 30% w/v in DI water, pH=5) was warmed to 50° C. A hole was drilled in the screw-cap of the centrifuge tube containing the Fab protein/colloidal gold solution, and 700 µl of the PEG solution, 5.25× protein weight, was added to the protein/colloidal gold solution while vortexing thoroughly during the addition and another five (5) seconds thereafter.

A slightly turbid solution was obtained and poured in a plastic Petri-dish. The dish was covered and placed at −20° C. for 1.5 hour, and then on dry ice for 30 minutes. The initially glossy appearance of the PEG/protein suspension became matted and solid. The frozen suspension was then lyophilized in a vacuum oven at room temperature over night.

Following lyophilization, PEG was extracted using chloroform. Once no soft spots were observed, the dry cake was transferred to a 50 ml centrifuge tube. A 20 ml aliquot of chloroform was added. The PEG dissolved, rendering a cloudy fine protein suspension. The chloroform was dispensed in 4 PTFE filters 0.2 um (Amicon, Ultrafree-CL) and centrifuged at 5500 rpm, 10° C. for 15 minutes. Using glass pipettes, fresh chloroform was added. This washing procedure was done 3 times in total. The protein particles were resuspended in 10 ml chloroform.

The colloidal gold-Fab microparticles were utilized in the following Examples 14B-1D.

14B. APTAC-EITC-PEI Coating

For the Examples, APTAC-EITC-PEI was prepared as described in Examples 1-2 in U.S. Patent Publication No. 2004/0202774, Chudzik, et al., "Charged Initiator Polymers and Methods of Use."

Batches of the prepared colloidal gold-Fab microparticles were prepared by suspending 4 mg of the microparticles in 1 ml chloroform. The suspensions were placed in centrifuge tubes. To the particles, 10, 25, 50 or 100 µl of a solution containing 2 mg/ml APTAC-EITC-PEI in methanol (MeOH) was added. Appropriate amounts of methanol were added to obtain a 10:1 chloroform/methanol mixture in each of the samples. The mixtures were incubated at room temperature for 20 minutes. The solutions became colorless and the particles were visibly coated with APTAC-EITC-PEI.

Any excess APTAC-EITC-PEI was removed by spinning the particles in PTFE filters (0.2 µm (Amicon, Ultrafree-CL)) at 3000 rpm for 3 minutes. Particles were then rinsed using $CHCl_3$ and spinning again at 3000 rpm for 3 minutes.

Next, solvent was removed from the particles by drying them in a vacuum oven. Particles were found insoluble when suspended in PBS. Over the course of 24 to 48 hours, the suspension slowly dissolved.

14C. Coating with APTAC-EITC-PEI and Polysaccharide

A 10 mg portion of colloidal gold-nucleated Fab particles was placed in a centrifuge filter. To the particles, 200 µl of a 2 mg/ml solution containing APTAC-EITC-PEI in methanol was added and incubated for 15 minutes. The solutions became colorless and the particles were visibly coated with APTAC-EITC-PEI. Any excess APTAC-EITC-PEI was removed by spinning the particles in PTFE filters (0.2 µm (Amicon, Ultrafree-CL)) at 3000 rpm for 3 minutes. Particles were then rinsed using $CHCl_3$ and spinning again at 3000 rpm for 3 minutes. Solvent was further removed from the particles by drying them in a vacuum oven.

The biodegradable polysaccharide utilized was a methacrylated maltodextrin (MD-methacrylate). To provide MD-methacrylate, the following procedure was performed. Maltodextrin (MD; Aldrich; 100 g; 3.67 mmole; Dextrose Equivalent (DE): 4.0-7.0) was dissolved in dimethylsulfoxide (DMSO) 1,000 ml with stirring. The size of the maltodextrin was calculated to be in the range of 2,000 Da to 4,000 Da. Once the reaction solution was complete, 1-methylimidazole (Aldrich; 2.0 g, 1.9 ml) followed by methacrylic-anhydride (Aldrich; 38.5 g) were added with stirring. The reaction mixture was stirred for one hour at room temperature. After this time, the reaction mixture was quenched with water and dialyzed against distilled (DI) water using 1,000 MWCO dialysis tubing. The MD-methacrylate was isolated via lyophilization to give 63.283 g (63% yield). The calculated methacrylate load of macromer was 0.33 mmoles/mg of polymer.

Coating solutions were made, using MD-methacrylate and polyethylene glycol (PEG, 30%), in concentrations of 500 µg/ml and 1 mg/ml. The coating solutions were added to the particles coated with APTAC-EITC-PEI. Particles were mixed thoroughly in suspension and placed under a UV light for 60 seconds using Blue Wave illuminator (DYMAX BLUE-WAVE 200 operating at 330 nm between about 1 and 2 $mW/cm^2$).

Particles were then spun down and excess coating solution was decanted.

14D. TEMED-DQ/Polysaccharide Coating

For this example, TEMED-DQ (Ethylenebis(4-benzoyl-benzyldimethylammonium)Dibromide (Diphoto-Diquat)) was prepared as described in U.S. Pat. No. 6,077,698, Swan et al., "Photoactivatable Cross-Linking Agents Containing Charged Groups for Water Solubility" (see Example 2).

Coating solutions for the prepared colloidal gold-Fab microparticles (Example 14) were prepared as follows. Generally, TEMED-DQ was found to be not readily soluble in chloroform, methanol or DDW at pH 7. Thus, TEMED-DQ, 10 mg was dissolved in solvent containing 100 µl of methanol and 900 ul of chloroform. A solution of 100 µl of the 1:9 MeOH.$CHCl_3$ was added to 5 mg of Fab particles (prepared in Example 14A). The mixture was allowed to react at room temperature for 30 minutes.

The microparticles were then dried in the vacuum oven until solvent was evaporated. A second coating solution was prepared dissolving MD-methacrylate in a 30% w/v PEG 20 kDa solution in DDW at pH 7, at concentrations of 500 µg/ml, 1 mg/ml or 50 mg/ml. MD-methacrylate/PEG solution, 1 ml, was added to the particles coated with TEMED-DQ. Particles were mixed thoroughly and then placed under the UV lamp for 60 seconds using Blue Wave illuminator (DYMAX BLUE-WAVE 200 operating at 330 nm between about 1 and 2 mW/cm$^2$).

After illumination, particles were spun down and excess MD-methacrylate/PEG solution was decanted.

Example 15

Formation of Fab Microparticles with Amphiphilic Polymer Coating

Microparticles were coated with APTAC-EITC-PEI as described in Example 14A above (4 mg colloidal gold-Fab microparticles with 0.2 mg APTAC-EITC-PEI). The coated particles were dried as described in Example 14A. The coated colloidal gold-Fab microparticles were resuspended in 1 ml of chloroform in a microcentrifuge tube.

For this Example, Poly(ethylene glycol)-di(imidazolyl carbonate) (PEG-DCI) was synthesized as described in co-pending application Ser. No. 11/789,786, filed Apr. 25, 2007, Jelle et al., and published as U.S. 2008/0039931 (see Example 7).

PEG-DCI was added to the particles in the following ways:
Samples 1-3. An aliquot of PEG-DCI (100 µl) was dissolved in 500 ml chloroform. 30 µl, 100 µl, or 230 µl of the resulting PEG-DCI/chloroform solution was added to the particles, and the particles were maintained at room temperature and monitored for dissolution in water regularly.
Sample 4. Dry APTAC-EITC-PEI-coated colloidal gold-Fab particles were resuspended in pure PEG-DCI (200 µl).
Sample 5a. Alternatively Fab-microparticles were coated with APTAC-EITC-PEI and subsequently with PEG-DCI in a one-pot reaction without removing the 30% w/v PEG that was present at the formation of the Fab particles after lyophilization.
Sample 5b. In duplicate, APTAC-EITC-PEI (0.2 mg) was added to the suspension of colloidal gold-Fab microparticles (4 mg) in chloroform where PEG 30% w/v was still present. After the particles were coated by APTAC-EITC-PEI and the solution had become colorless, PEG-DCI (200 µl) in 1 ml of chloroform was added.
The resulting coated particles (Samples 1-5b) were dried in a vacuum oven. Particles were found insoluble when suspended in PBS.

What is claimed is:

1. An elution control matrix for the controlled release of a hydrophilic bioactive agent, comprising a polymeric matrix comprising:
   a first polymer that is hydrophobic, wherein a portion or all of the polymeric matrix is formed from the first polymer; and
   a plurality of microparticles dispersed within the polymeric matrix; wherein the microparticles comprise a hydrophilic bioactive agent and crosslinked hydrophilic polymer.

2. The elution control matrix of claim 1 wherein the microparticles comprise a polypeptide.

3. The elution control matrix of claim 1, wherein the microparticles comprises a polypeptide that is an antibody or fragment thereof.

4. The elution control matrix of claim 1, wherein the microparticles comprises a Fab fragment.

5. The elution control matrix of claim 1, wherein the microparticles are formed predominantly of the hydrophilic bioactive agent.

6. The elution control matrix of claim 1 wherein the first polymer is a biostable polymer.

7. The elution control matrix of claim 6 wherein the first polymer is selected from the group consisting of poly(alkyl (meth)acrylates) and poly(aromatic(meth)acrylates).

8. The elution control matrix of claim 7 wherein the first polymer comprises poly(n-butyl methacrylate).

9. The elution control matrix of claim 1 further comprising a second polymer that is biodegradable.

10. The elution control matrix of claim 1 further comprising a second polymer, wherein the weight ratio of the second polymer to the microparticles in the matrix is in the range of 0.5:1 to 1:1.

11. The elution control matrix of claim 1 wherein the crosslinked hydrophilic polymer comprises a polysaccharide.

12. The elution control matrix of claim 11 wherein the crosslinked hydrophilic polymer comprises a polysaccharide selected from the group consisting of maltodextrin and amylose.

13. The elution control matrix of claim 1 wherein the microparticles are present in the matrix in an amount in the range of 30% to 70% by weight solids.

14. The elution control matrix of claim 1 wherein the microparticles are present in the matrix in an amount in the range of 30% to 40% by weight solids.

15. The elution control matrix of claim 1 which is in the form of a coating on an implantable medical device.

16. The elution control matrix of claim 1 which is in the form of a coating on an implantable intraocular device.

17. The elution control matrix of claim 1 wherein the hydrophilic polymer is crosslinked on the surface of the particle forming a coating or shell.

18. The elution control matrix of claim 1 wherein the crosslinked hydrophilic polymer is crosslinked via polymerized groups pendent from the hydrophilic polymer.

19. The elution control matrix of claim 1 wherein the crosslinked hydrophilic polymer is crosslinked via polymerized groups pendent from the hydrophilic polymer, wherein crosslinking is performed using a polymeric polymerization initiator comprising charged groups.

20. The elution control matrix of claim 1 which is in the form of an implant.

21. The elution control matrix of claim 1 wherein the first polymer is soluble in a halogenated alkane solvent.

* * * * *